United States Patent
Robinson et al.

(10) Patent No.: US 11,234,737 B2
(45) Date of Patent: Feb. 1, 2022

(54) CIRCULAR FIXATOR SYSTEM AND METHOD

(71) Applicant: Wright Medical Technology, Inc., Memphis, TN (US)

(72) Inventors: Chris Robinson, Hernando, MS (US); Kian-Ming Wong, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

(21) Appl. No.: 16/822,265

(22) Filed: Mar. 18, 2020

(65) Prior Publication Data

US 2021/0153903 A1 May 27, 2021

Related U.S. Application Data

(63) Continuation of application No. 15/773,665, filed as application No. PCT/US2016/055747 on Oct. 6, 2016, now Pat. No. 10,624,674.

(Continued)

(51) Int. Cl.
*A61B 17/64* (2006.01)
*A61B 17/62* (2006.01)
(Continued)

(52) U.S. Cl.
CPC ............ *A61B 17/645* (2013.01); *A61B 17/62* (2013.01); *A61B 17/6425* (2013.01);
(Continued)

(58) Field of Classification Search
CPC ....... A61B 17/62; A61B 17/64; A61B 17/645; A61B 17/6458; A61B 17/6425; A61F 5/0195
(Continued)

(56) References Cited

U.S. PATENT DOCUMENTS 5,540,686 A * 7/1996 Zippel ................ A61B 17/6441
606/56
5,863,292 A * 1/1999 Tosic ..................... A61B 17/66
606/56

(Continued)

FOREIGN PATENT DOCUMENTS

EP 2417923 A1 2/2012
EP 2777565 A1 9/2014
(Continued)

OTHER PUBLICATIONS

Extended European Search Report issued in connection with European Patent Application No. 16864733.7, dated Jun. 24, 2019, 7 pages.

(Continued)

*Primary Examiner* — Eduardo C Robert
*Assistant Examiner* — Christina Negrellirodriguez
(74) *Attorney, Agent, or Firm* — Duane Morris LLP

(57) ABSTRACT

A device includes a plurality of rings. Each ring has a first face, a second face, and at least one slot defined by first and second interior edges of the ring on opposing sides of the slot. The at least one slot penetrates from the first face to the second face. The first face of each ring has a first recess adjacent the slot on the first edge and a second recess adjacent the slot on the second edge. A plurality of posts join each one of the plurality of rings to an adjacent one of the plurality of rings.

8 Claims, 38 Drawing Sheets

Related U.S. Application Data

(60) Provisional application No. 62/254,489, filed on Nov. 12, 2015.

(51) Int. Cl.
*A61F 5/01* (2006.01)
*A61B 17/17* (2006.01)
*A61B 17/88* (2006.01)
*A61B 17/00* (2006.01)

(52) U.S. Cl.
CPC ........ *A61F 5/0195* (2013.01); *A61B 17/1796* (2013.01); *A61B 17/8897* (2013.01); *A61B 2017/00407* (2013.01)

(58) Field of Classification Search
USPC .............................................. 606/54, 56–59
See application file for complete search history.

(56) References Cited

U.S. PATENT DOCUMENTS

| | | | |
|---|---|---|---|
| 5,997,537 | A | 12/1999 | Walulik |
| 8,192,434 | B2 | 6/2012 | Huebner et al. |
| 8,945,128 | B2 * | 2/2015 | Singh ..................... A61B 17/66 606/54 |
| 9,101,398 | B2 | 8/2015 | Singh |
| 2005/0059968 | A1 | 3/2005 | Grant et al. |
| 2012/0232554 | A1 | 9/2012 | Shaevitz et al. |
| 2015/0094721 | A1 | 4/2015 | Singh et al. |

FOREIGN PATENT DOCUMENTS

| | | |
|---|---|---|
| WO | WO9812975 A2 | 4/1998 |
| WO | 2015167581 A1 | 11/2015 |

OTHER PUBLICATIONS

Office Action issued in connection with Canadian Patent Application No. 3,004,736, dated Mar. 19, 2019, 5 pages.
First Examination Report issued in connection with corresponding Australian Patent Application No. 2016351551, dated Oct. 24, 2018 3 pages.
International Search Report and Written Opinion issued for PCT/US2016/055747, dated Jan. 11, 2017.

* cited by examiner

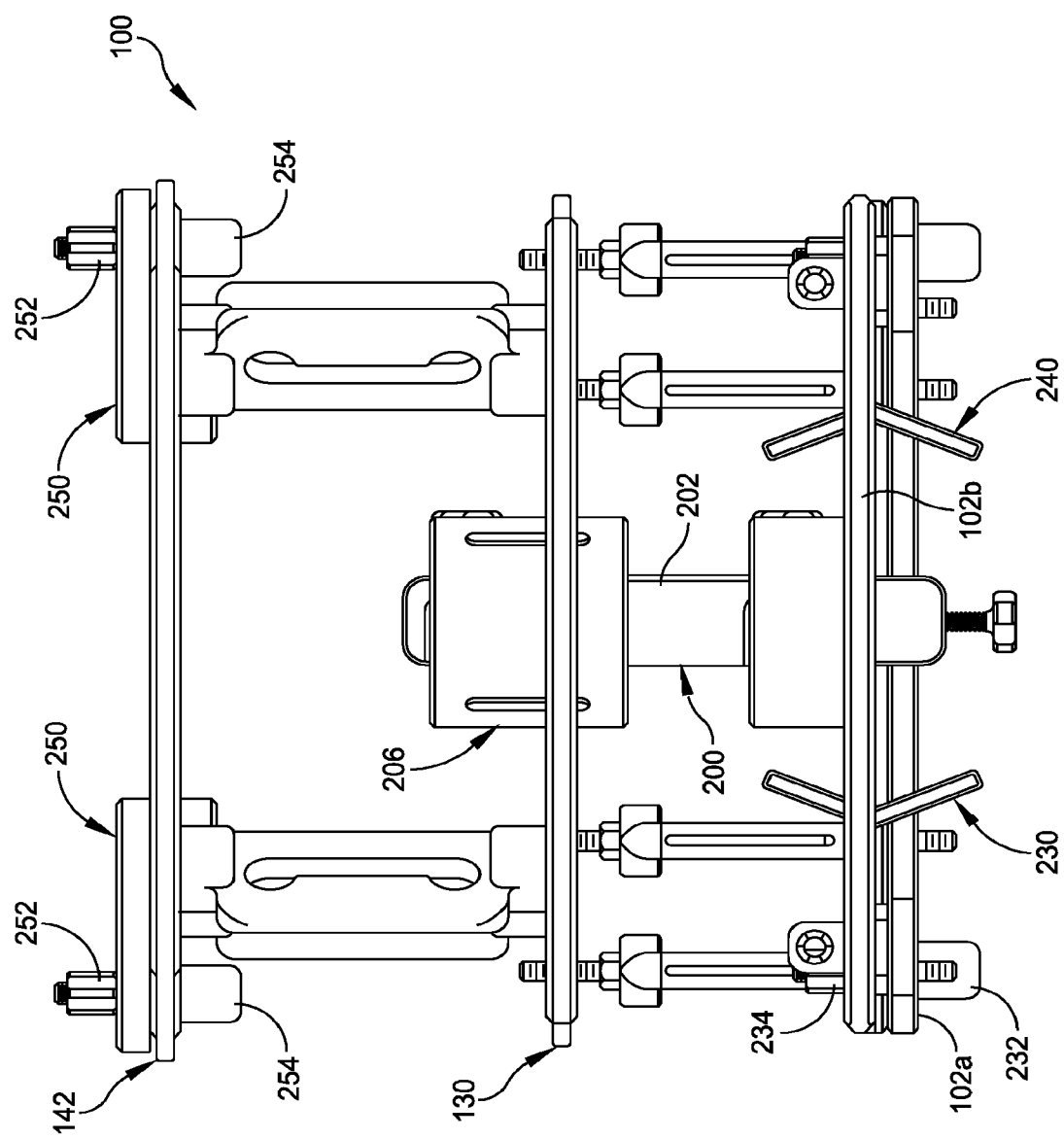

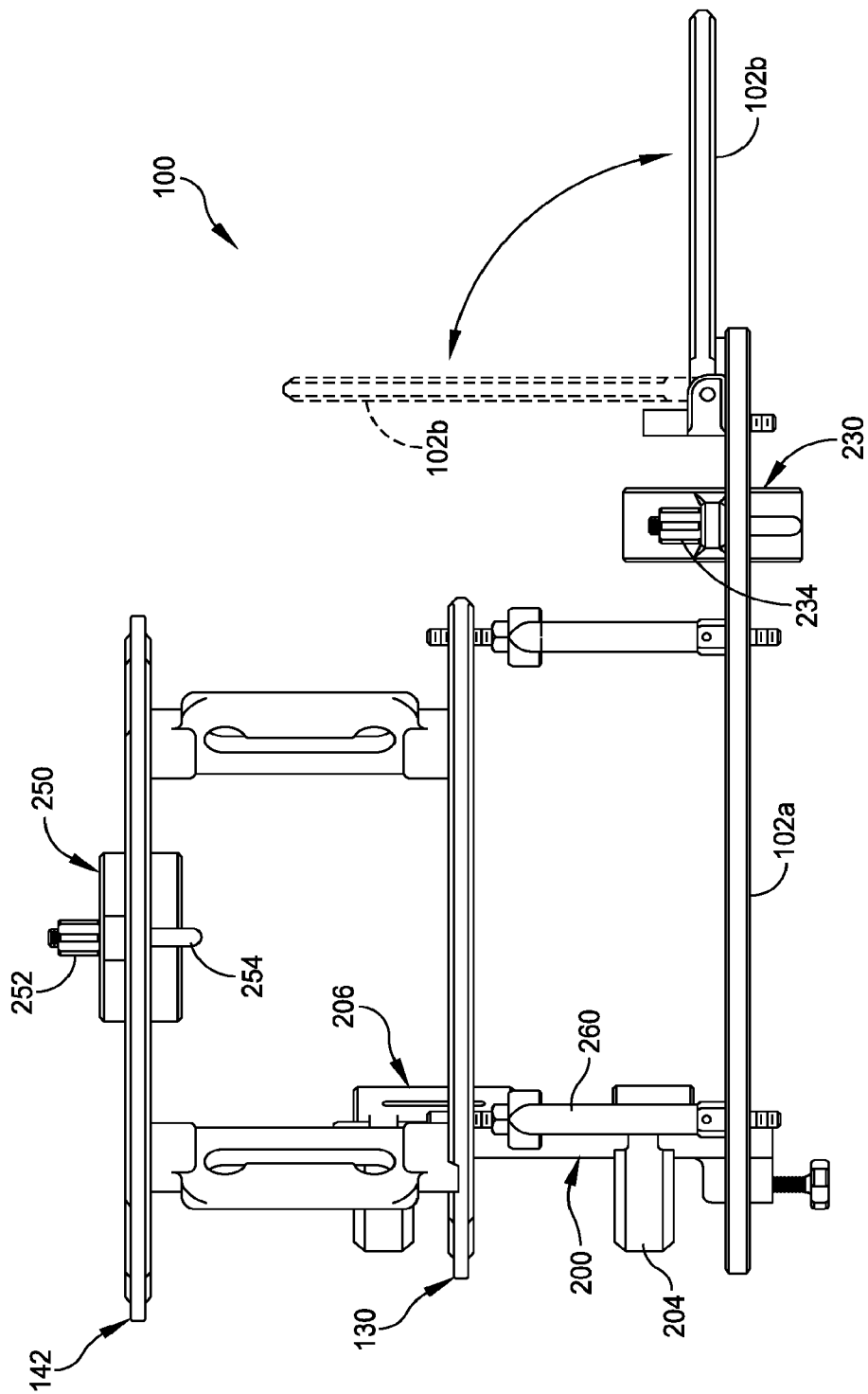

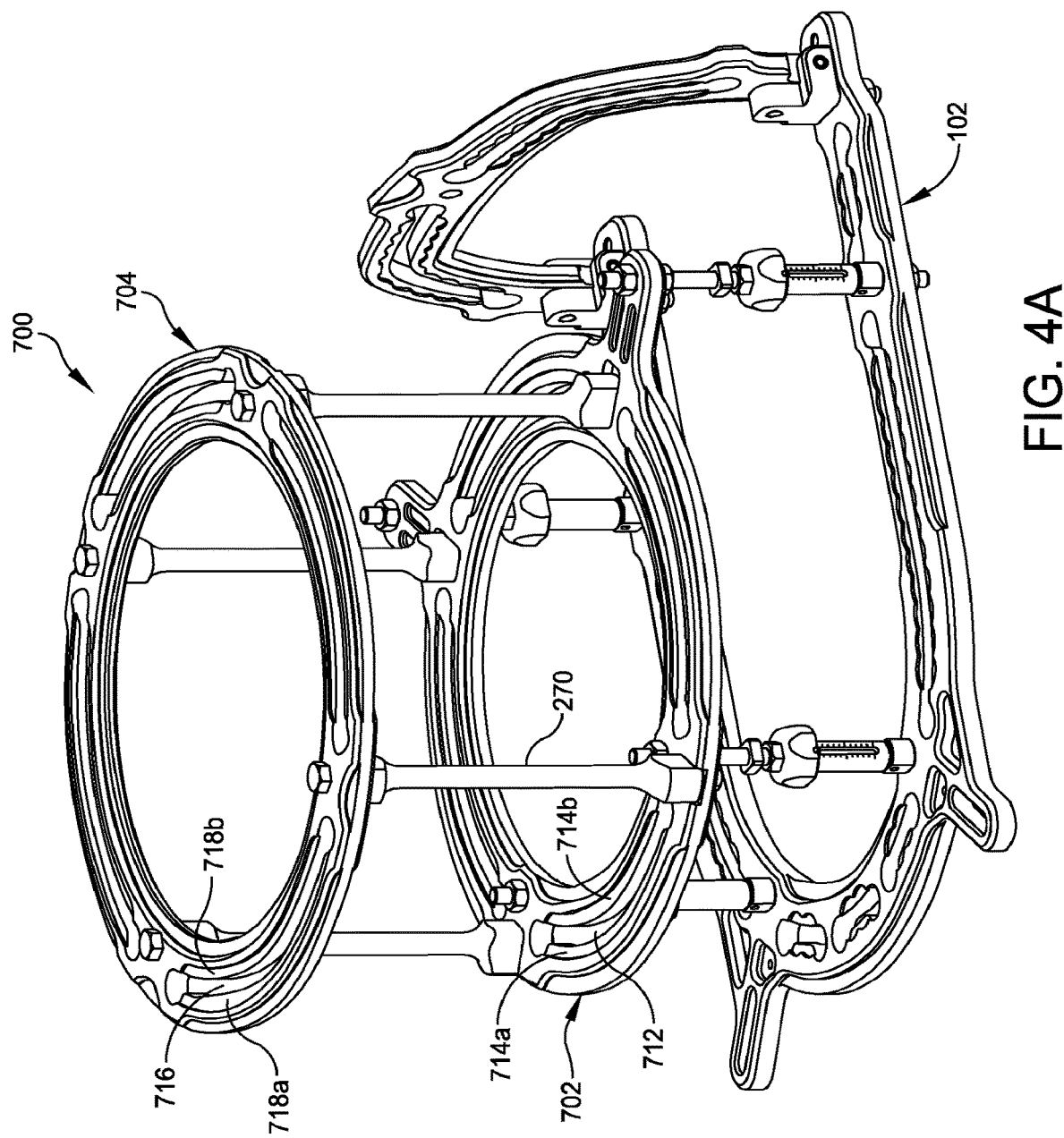

CIRCULAR FIXATOR SYSTEM AND METHOD

This application is a continuation of U.S. patent application Ser. No. 15/773,665, filed May 4, 2018, which is a national phase entry under 35 U.S.C. § 371 of international patent application no. PCT/US2016/055747, filed Oct. 6, 2016 which claims the benefit of priority of U.S. Provisional Patent Application No. 62/254,489, filed Nov. 12, 2015, all of which are expressly incorporated herein by reference in their entireties.

FIELD

This application pertains generally to medical devices, and more particularly to a circular fixator.

BACKGROUND

For most standard triple arthrodesis procedures, a prebuilt frame including two tibial rings and a foot plate with an extension can be utilized. A Circular Fixator system can be used for open or closed fracture fixation, pseudoarthrosis or nonunions of long bones, limb lengthening by epiphyseal or metaphyseal distraction, correction of bony or soft tissue deformities, or correction of segmental or nonsegmental bony or soft tissue defects. Circular Fixators have been used on long bones including: the tibia, fibula, femur, humerus, radius and ulna.

Prior to insertion of wires or pins, the circular fixator is positioned around the tibia and foot. The leg is eccentrically located in the frame to accommodate the posterior musculature, and the plantar aspect of the foot extends above or below the foot plate. To maintain the tibia and foot in position, folded up towels can be placed under the calf.

The surgeon inserts wires through the bones, and secures the wires to the frame using bolts that are inserted into holes in the rings and foot plate of the frame.

BRIEF DESCRIPTION OF THE DRAWINGS

FIG. 2B is a posterior side elevation view of the circular fixator of FIG. 1A.

FIG. 3 is a side elevation view of the circular fixator of FIG. 1A.

FIG. 4A is an isometric view of a variation of the circular fixator of FIG. 1A having recess pockets (without scallops).

FIG. 15.

DETAILED DESCRIPTION

Figure 1A:
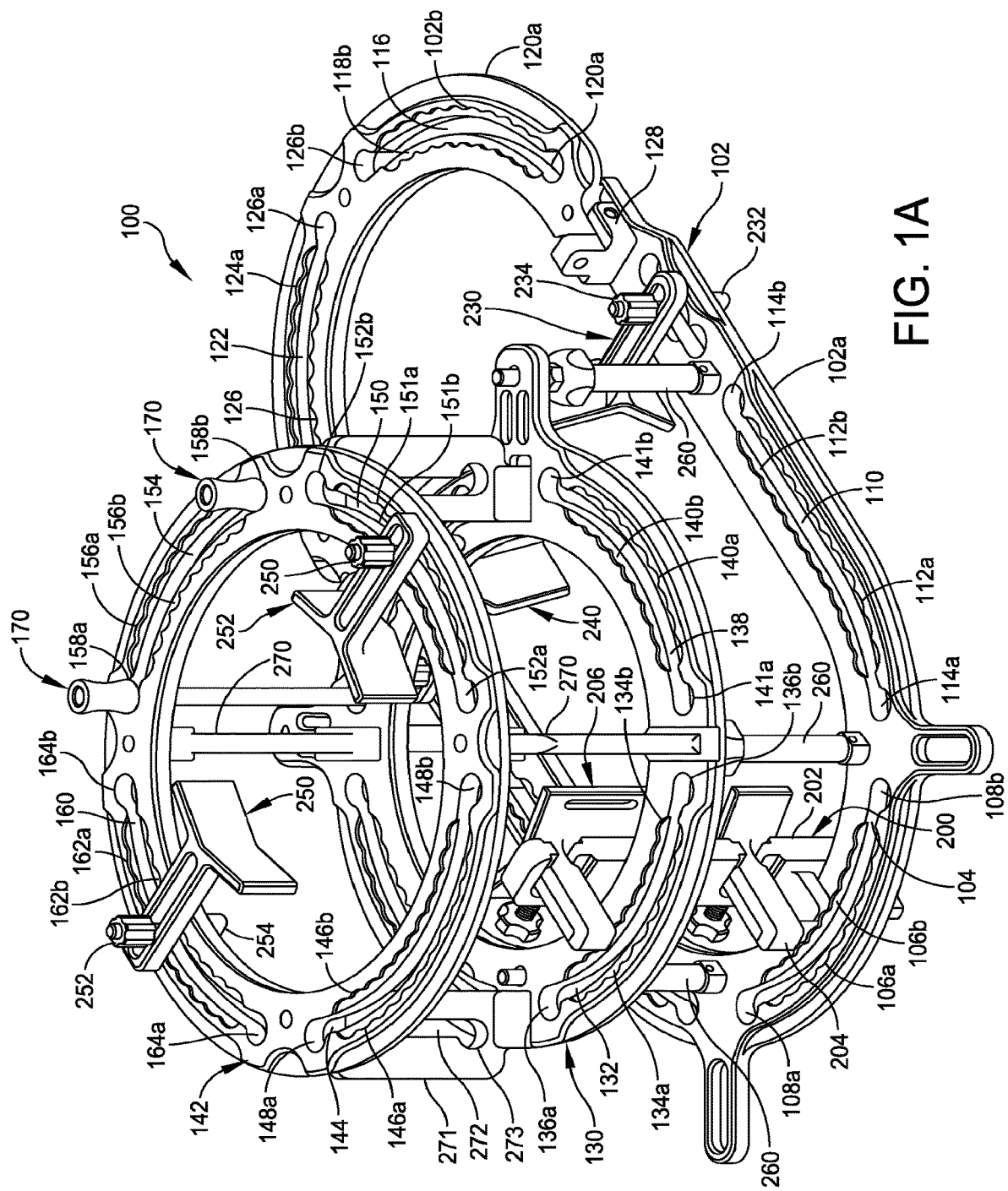
FIG. 1A is an isometric view of a circular fixator according to some embodiments.

This description of the exemplary embodiments is intended to be read in connection with the accompanying drawings, which are to be considered part of the entire written description. In the description, relative terms such as "lower," "upper," "horizontal," "vertical,", "above,"

"below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present disclosure provides circular fixators comprising rings with a plurality of slots for attachments of fixation devices. The fixation devices fix the wires that inserted into the patient's leg and/or foot, for example. The circular fixator can be used for other extremities with different variations of the structures as described herein. In some embodiments, the fixation devices include bolts with side slots, for receiving the wires. The fixation devices can be pre-assembled and pre-loaded onto the circular fixator (e.g., by a scrub technician) prior to the arrival of the surgeon in the operating room. After inserting the wire, the surgeon can quickly and easily slide the pre-loaded fixation device into position for capturing the wire in a side slot of the fixation device. In some embodiments, the rings have recesses. The recesses can include receptacles such as scallop-shaped recesses, curved recesses, V-shaped recesses, rectangular, semi-hexagonal, semi-octagonal, or recess pockets on both sides of the slots, and recesses adapted to receive the fixation devices, and prevent them from slipping in the tangential direction when the surgeon applies tension to the wires for compression or distraction of joints or fractures. In some embodiments, the fixation devices include washers adapted to fit in respective recesses. The fixation device is configured to fit in the receptacle. In some embodiments, at least one edge of the fixation device can be received by the receptacle, even though the shape of the fixation device is different from the shape of the receptacle. For example, a rectangular receptacle can receive a hexagonal fixation device, and two sides of the receptacle will engage two opposite sides of the hexagonal fixation device to prevent slippage.

In some embodiments, one or more of the fixation devices include posts for providing an offset between the plane of the ring and the fixation bolt. In some embodiments, the posts have horizontal grooves and the washer has a ridge for engaging one of the grooves of the post, to prevent the bolt from slipping on the post. In some embodiments, the posts are adapted to fit in the recesses.

In some embodiments, leg positioners are provided for supporting the leg and foot in a neutral position or other desired position during the procedure. In some embodiments, the leg positioners can be positioned and affixed to the circular fixator quickly and easily without using any tools, and the leg positioners have support elements, which can be quickly and easily adjusted without using tools for positioning the leg.

Figure 1B:
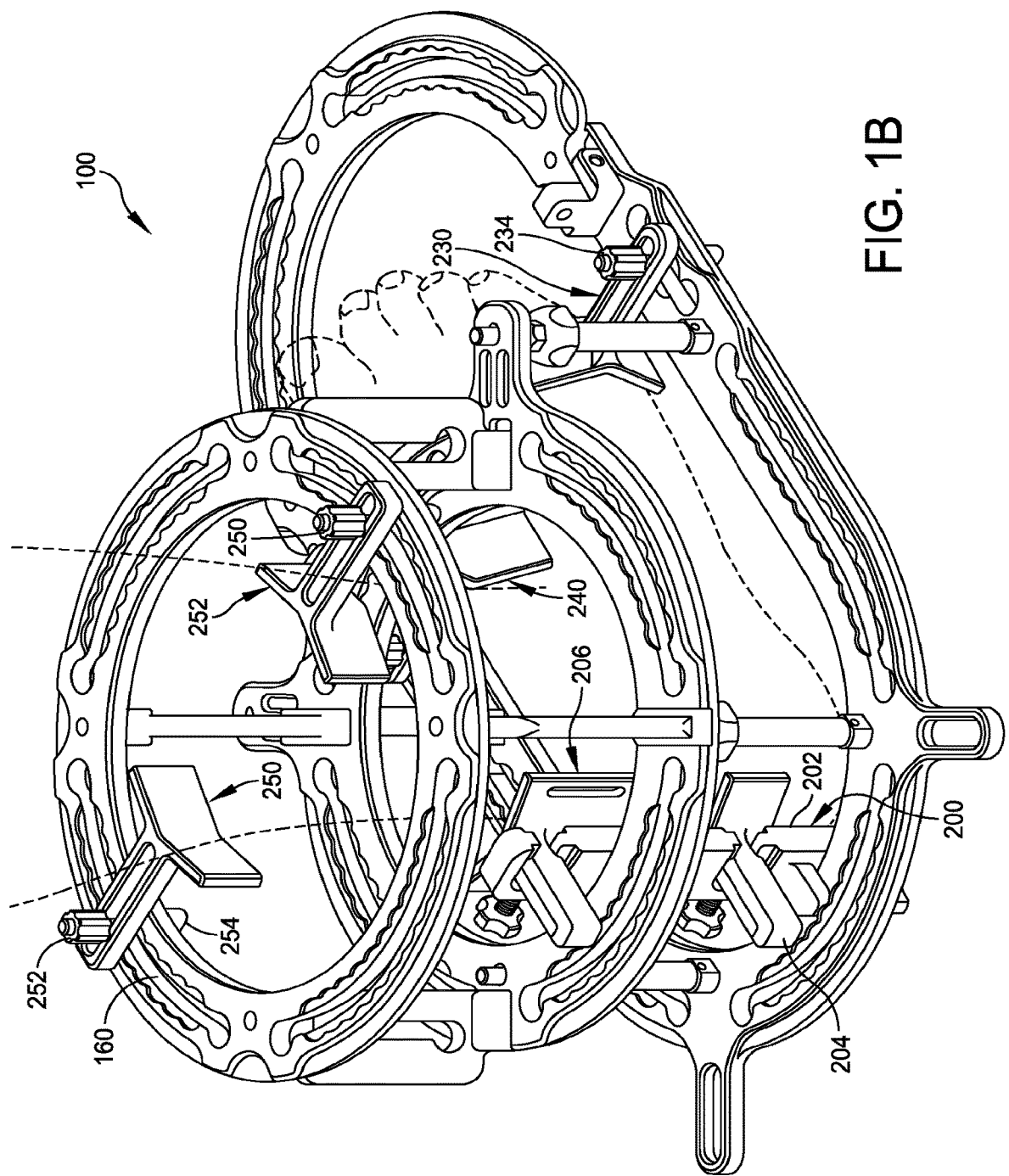
FIG. 1B shows a patient's leg positioned in the circular fixator of FIG. 1A.
Figure 1C:
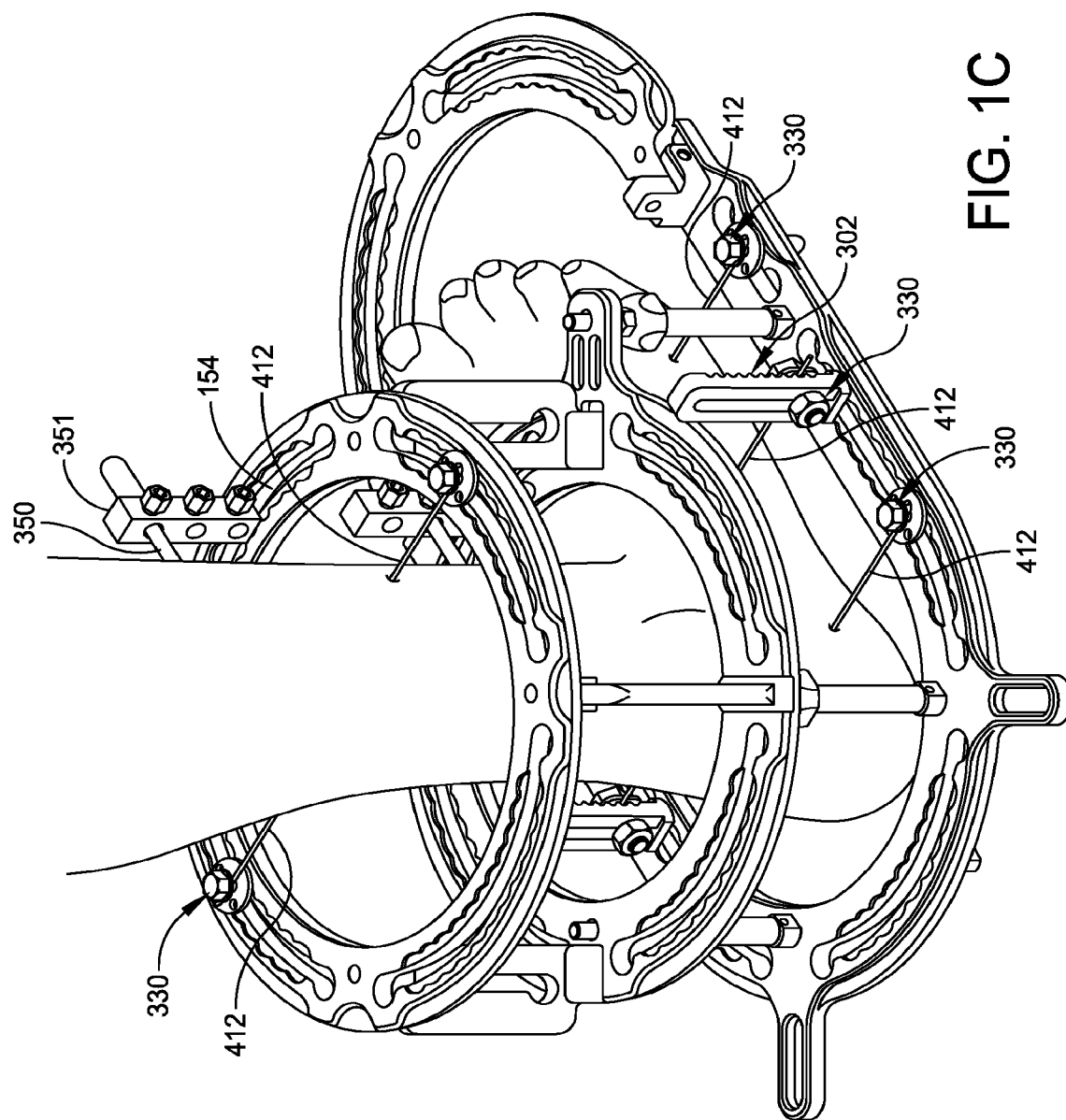
FIG. 1C shows the patient's leg fixed in the circular fixator of FIG. 1A.
Figure 2A:
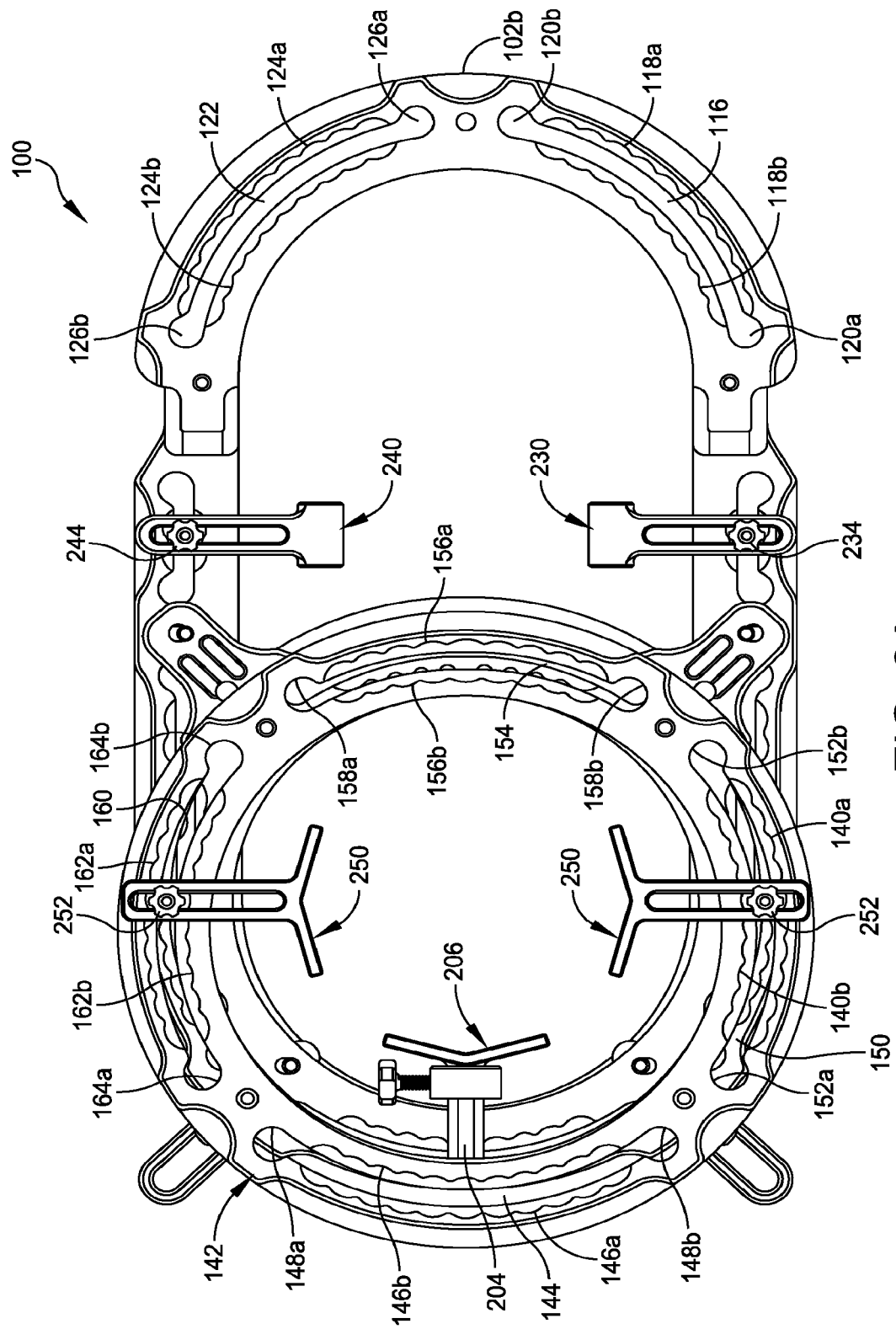
FIG. 2A is a plan view of the circular fixator of FIG. 1A.

FIG. 1A is a an isometric view of a circular fixator 100 according to some embodiments of this disclosure. FIG. 1B shows the circular fixator 100 of FIG. 1A with a patient's foot drawn in phantom to show an exemplary use of the circular fixator for positioning the leg prior to and during the fixation procedure. FIG. 1C shows the circulator fixator 100 with the patient's foot fixed by wires 412, following the procedures. FIGS. 2A, 2B and 3 show plan, rear elevation and side elevation views of the circular fixator 100.

The circular fixator 100 is a device comprising a plurality of rings 102, 130 and 142. In some embodiments, one ring 102 of the plurality of rings is elongated. The elongated ring 102 has a proximal portion 102a and a distal portion 102b. The elongated ring 102 is configured so that the distal portion 102b can be rigidly attached to the first portion 102a in a first position parallel to or coplanar with the proximal portion 102a. As shown in phantom in FIG. 3 the distal portion 102b can be rigidly attached to the first portion 102a in a second position having a non-zero angle with respect to the proximal portion. In some embodiments, the non-zero angle is 90 degrees.

In some embodiments, the plurality of rings include first and second circular rings 142, 130 adapted to be positioned around a leg of a patient during fixation, and the first ring 142 is greater in diameter than the second ring 130 and 102. This configuration permits the surgeon to maintain a constant distance. As a general rule of thumb, the clearance between the inner diameter of each ring and the nearest leg tissue is about two fingers' breadth (e.g., about 3.7 cm to about 4 cm), at different heights along the patient's leg. Similarly, if the fixator is adapted for use on another extremity, a similar clearance between the inner diameter of each ring and the nearest tissue is used. Because the patient's calf is greater in diameter further from the ankle, the top ring 142 is correspondingly greater in inner diameter than the middle ring 130. Because the ring 130 is smaller, it reduces the moment arm for pins or wires. For example in one embodiment, the top ring 142 has an inner diameter of about 18 cm, and the middle ring 130 has an inner diameter of about 16 cm. This is just one example, and any combination of ring sizes can be used to accommodate the geometry of any given patient's calf.

Each ring 102, 130 and 142 has a first (e.g., top) face, a second (e.g., bottom) face, and at least one slot. For example, ring 102 has slots 104, 110, 116, 122; ring 130 has four slots, including slots 132, 138; and ring 142 has slots 144, 150, 154, and 160. Each slot is defined by first and second interior edges of its respective ring 102, 130 and 142 on opposing sides of the slot. Each slot (e.g., 104) penetrates from the first face of the ring (e.g., 102) to the second face. The first (e.g., top) face of each ring (e.g., 102) has a first scallop-shaped recess (e.g., 106a) adjacent the slot 104 on the first edge and a second scallop-shaped recess (e.g., 106b) adjacent the slot 104 on the second edge. The slot 104 terminates at an opening 108a, 108b at each respective end of the slot. The openings 108a, 108b have a dimension that is substantially greater than a width of the slot 106. Similarly, in the example of FIG. 1, slot 110 has scallop-shaped recesses 112a, 112b and end openings 114a, 114b; slot 116 has recesses 118a, 118b and end openings 120a, 120b; slot 122 has recesses 124a, 124b and end openings 126a, 126b; slot 132 has recesses 134a, 134b and end openings 136a, 136b; slot 138 has recesses 140a, 140b and end openings 141a, 141b; slot 144 has recesses 146a, 146b and end openings 148a, 148b; slot 150 has recesses 151a, 151b and end openings 152a, 152b; and slot 160 has recesses 162a, 162b and end openings 164a, 164b.

In other embodiments, instead of a scallop-shaped recess 134a, 134b, 146a, 146b, one or more of the rings include recess pockets, as described below with reference to FIGS. 4A and 4B. In some embodiments the circular fixator includes at least one ring 102 having scallop shaped recesses 106a, 106b, 112a, 112b, 118a, 118b, and at least one ring having recess pockets, as described below in the discussion of FIG. 4A.

Figure 4B:
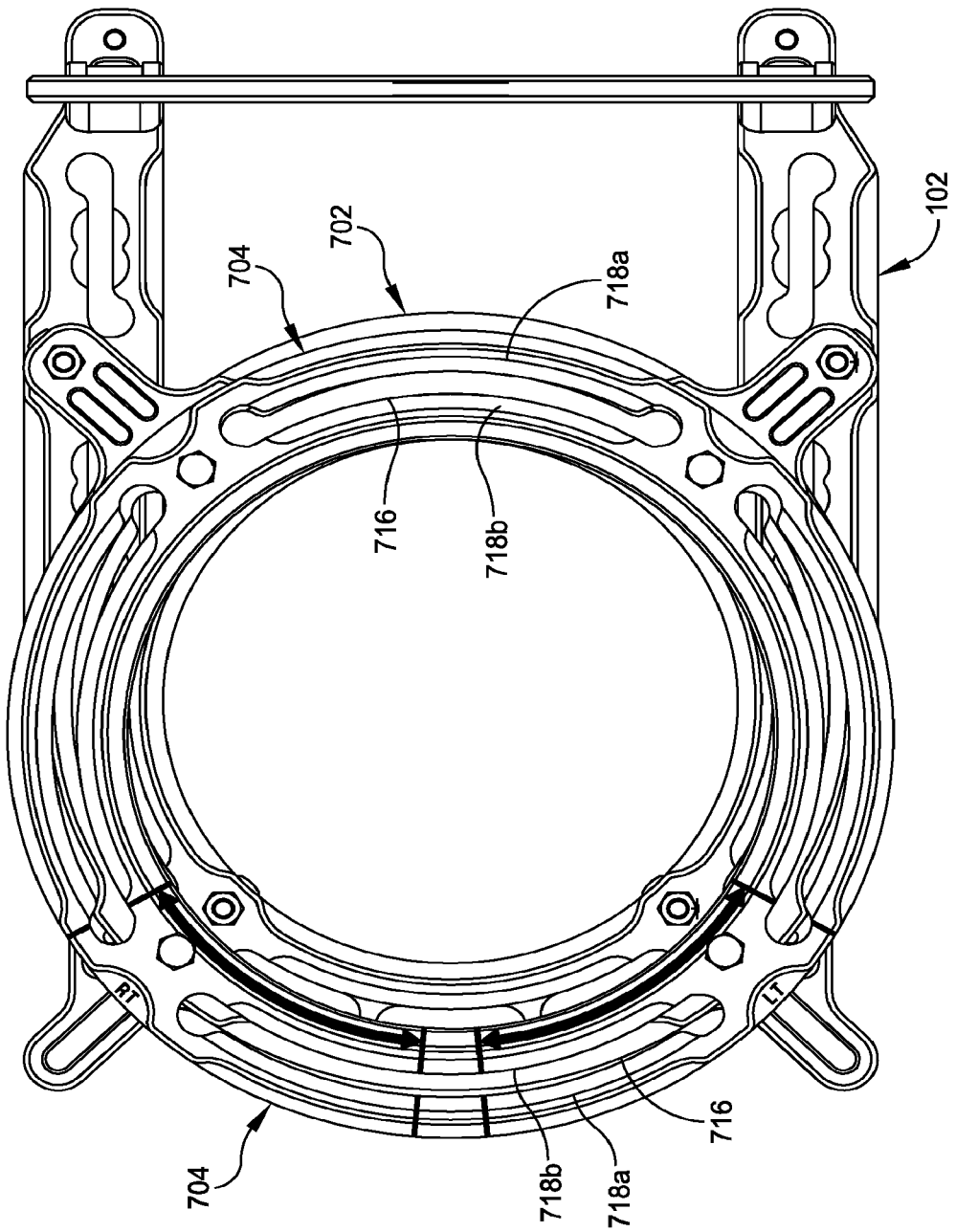
FIG. 4B is a plan view of the device of FIG. 4A.

FIGS. 4A and 4B show a variation of the circular fixator 700. In some embodiments, the circular fixator 700 includes the same bottom ring 102 as described above, with scalloped recesses on each side of each slot. The scallops provide additional protection against slippage of the fixation device, for example when tensioning a wire to compress or distract a joint. In some embodiments, the middle ring 702 has slots 712 with recesses 714a, 714b (without scallops) on each side of the slots 712. Similarly, the top ring 704 has slots 716 with recesses 718a, 718b (without scallops) on each side of the slots 712. In many procedures, the surgeon does not require compression or distraction of the foot or leg at the levels of the middle ring 702 or the top ring 704. These rings 702, 704 stabilize the leg. The rings 130, 142 with scallops can be used at the upper levels of the leg as described above with reference to FIGS. 1-3.

However, if the upper and middle ring are only used for stabilization, the rings 702, 704 without the scallops may permit the fixation device 300 to move toward the wire more quickly without any chance of becoming caught in a scallop. Additionally, the recesses 714a, 714b, 718a, 718b without scallops allow the surgeon to fix the fixation device 300 anywhere along the length of the slots, and the surgeon is not limited to any discrete set of fixed locations.

When the wire is run perpendicular to the slots 712, 716, there is little chance that the fixation device 300 can slip in the slot. If the wires are to be run perpendicular or nearly perpendicular to the slots, the surgeon may prefer that the rings 702, 704 (without scallops) are used for ease of use. On the other hand, the greater the angle between the wires and the slots, the greater the benefit of the scallops, for preventing slippage.

In other embodiments (not shown), all three rings 102, 702, 704 can be provided without scallops.

The reference numerals of other features of the circular fixator of FIGS. 4A and 4B which are the same as the corresponding items shown in FIG. 1A are omitted for ease of understanding, and their descriptions are not repeated.

The device further includes a plurality of posts 270 joining each one of the plurality of rings 130, 142 to an adjacent one of the plurality of rings. In some embodiments, the center ring 130 is connected to the top ring 142 by fixed posts 270, and the center ring 130 is connected to the bottom ring 102 by a plurality of calibrated struts 260. The calibrated struts permit accurate and even adjustments to the distance between the bottom ring 102 and the center ring 130 (e.g., for compression/distraction of the foot or height adjustments to the desired height). In some embodiments, all of the posts 270 are of the same fixed type (as shown in FIG. 4A). In some embodiments, as shown in FIG. 1A, one or more of the posts 270 can be replaced by suitably configured plates 271, threaded rods, spacers, or struts. For example, the places 271 can each have a respective vertical slot 272. Each slot 272 has openings 273 at the top and bottom of the slot. The slots 272 can have the same width as the slots 112a, 112b, and the openings 273 can have the same size as the openings 114a, 114b. The slots 272 of the plates 271 can receive fixations elements 330, and the openings 273 can receive plugs 170, for pre-loading the fixation elements 330, in the manner described below. In other embodiments, any combination of posts 270, plates 271, rods, spacers and/or struts can be used.

In some embodiments, each scallop-shaped recess (e.g., 112a, 112b) comprises a plurality of curved arcs, and each curved arc subtends an angle in a range from about 10 degrees to 170 degrees. In some embodiments, the subtended angle is in a range from 30 degrees to 150 degrees.

Figure 5:
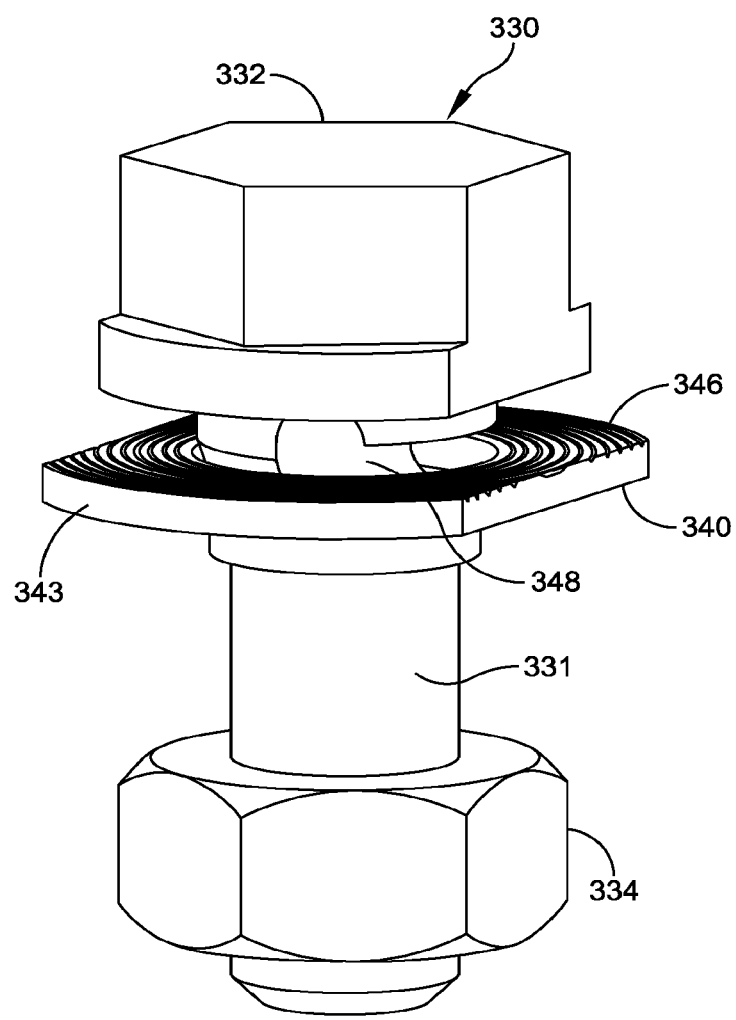
FIG. 5 is an isometric view of one of the fixation elements of FIG. 1C.
Figure 6:
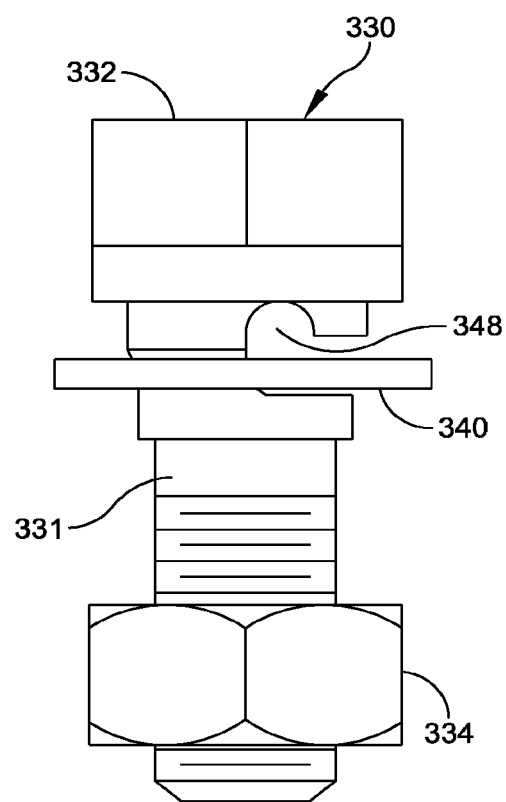
FIG. 6 is a side elevation view of the fixation element of FIG. 5.

In some embodiments, the subtended angle is in a range from 30 degrees to 150 degrees. In some embodiments, the subtended angle is in a range from 60 degrees to about 120 degrees. In some embodiments, each scallop-shaped recess comprises a plurality of circular arcs, each circular arc subtending an angle of about 90 degrees. The arcs subtend an angle that is sufficiently large to resist slipping of any fixation device 330 (FIG. 5, described below) relative to the slot, particularly if any force component is applied to the fixation device 330 parallel to the direction of the slot (e.g., 110). In some embodiments, the rings 102, 130, 142 comprise a metal, such as aluminum or titanium.

In some embodiments, at least one of the fixation devices 300 comprises a bolt 330, a nut 334 and a washer 340. The bolt 330 has head 332 and a threaded portion 331 sized to fit through the slot (e.g., 112a, 112b). The bolt 330 includes a side slot 348 in a side surface of the threaded portion 331, for receiving a wire (FIG. 1C) The washer 340 is shaped to fit a respective one of the curved arcs on the scallop-shaped recess 114a, 114b on each side of the slot 110 of the ring 102. In some embodiments, the washer 340 has a textured gripping surface 346 for securely positioning the wire. The washer 340 has two curved edges 343 adapted for fitting the curved arcs of the scallop shaped recesses. The remaining two edges of the washer can be flat. The gripping surface can have ridges, barbs, splines, slots, a knurled surface, or the like. In some embodiments, the opening (e.g., 114a, 114b) at each end of each slot (e.g., 112a, 112b) is adapted to receive a nut 334 of a fixation device 330 through the opening. In some embodiments, the slot (e.g., 112a, 112b) is adapted to receive a threaded portion 331 of the fixation device 330 through the slot, but the slot has a width that is smaller than a dimension of the nut 334. Thus, once the nut 334 is affixed to the threaded portion 331, the fixation device 330 can be inserted into the openings (e.g., 114a, 114b) but cannot fall out of the slots. The fixation devices can be pre-assembled, and the pre-assembled fixation devices can pre-loaded onto the slots prior to surgery. The openings (e.g., 114a, 114b) can be then be plugged to prevent release of the fixation devices 330.

Some embodiments further comprise at least one post 302 (FIG. 7) having a threaded body portion 314 adapted to fit through the slot (e.g., 110) of the ring 102. The post 302 has a longitudinal slot 307 (add to drawing) through the post (and parallel to the longitudinal axis of the post) for receiving the bolt 330 of the fixation device 300. The post 302 has a mounting surface 303 for engaging a respective one of the curved arcs on the scallop-shaped recess (e.g., 112a) on each side of the slot (110). In some embodiments, the mounting surface 303 of the post 302 has two curved (e.g., circular) arc edges 310, adapted to be received in one of the curved arcs on the scallop-shaped recess. In some embodiments, the mounting surface 303 of the post 302 has two flat edges 312, which can be gripped in the jaws of a wrench or other suitable tool. The post 302 allows the surgeon to position the bolt 330 of a fixation device 300 at a height that is offset from the rings 102, 130, 142.

Figure 7:
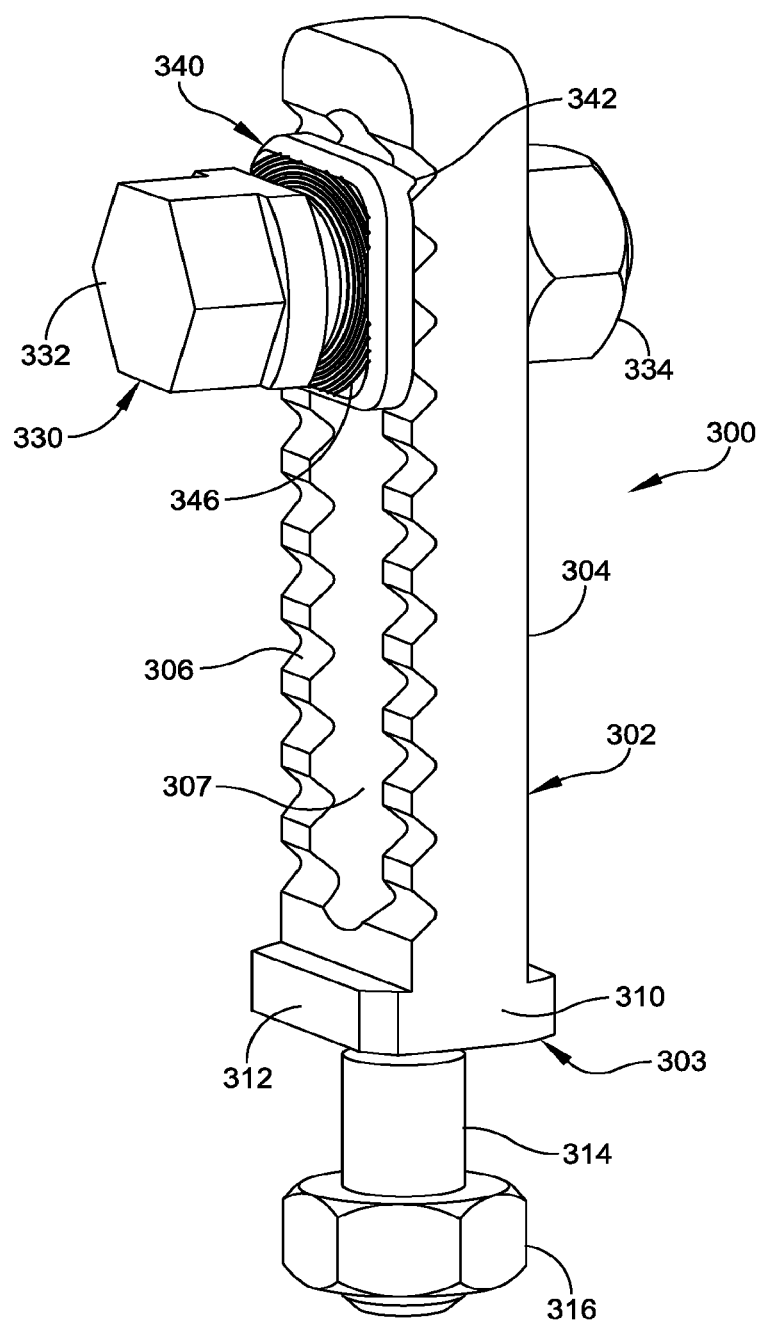
FIG. 7 is an isometric view of an embodiment of the fixation element further including a post.
Figure 8:
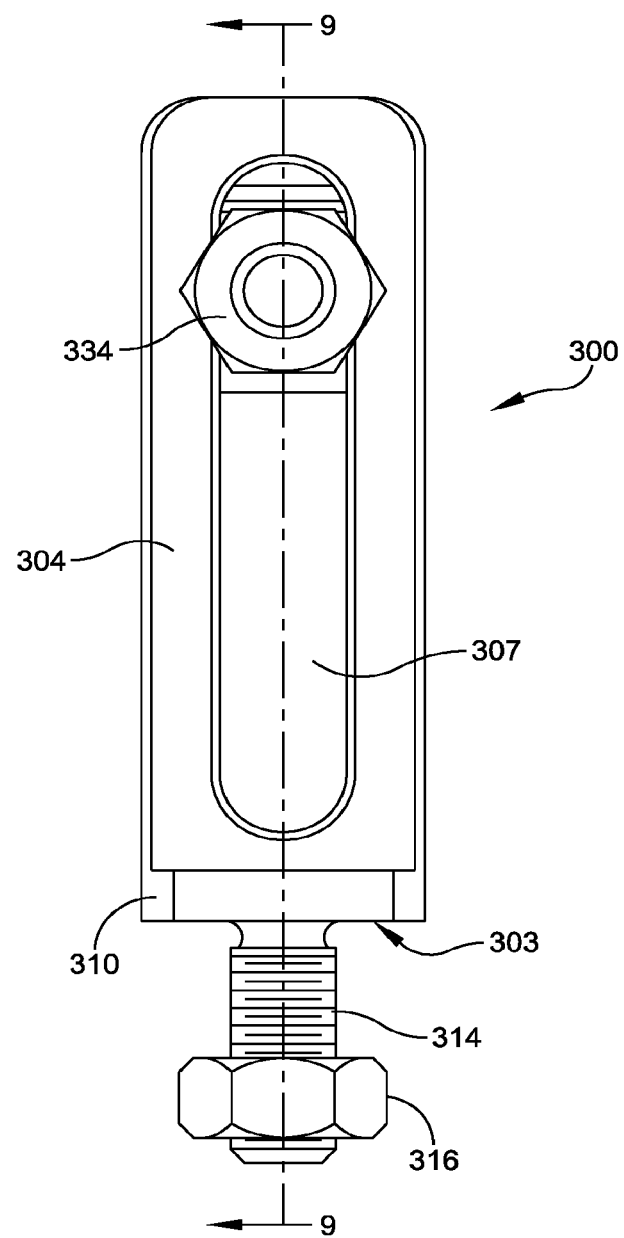
FIG. 8 is a front elevation view of the fixation element of FIG. 7.
Figures 9, 10:
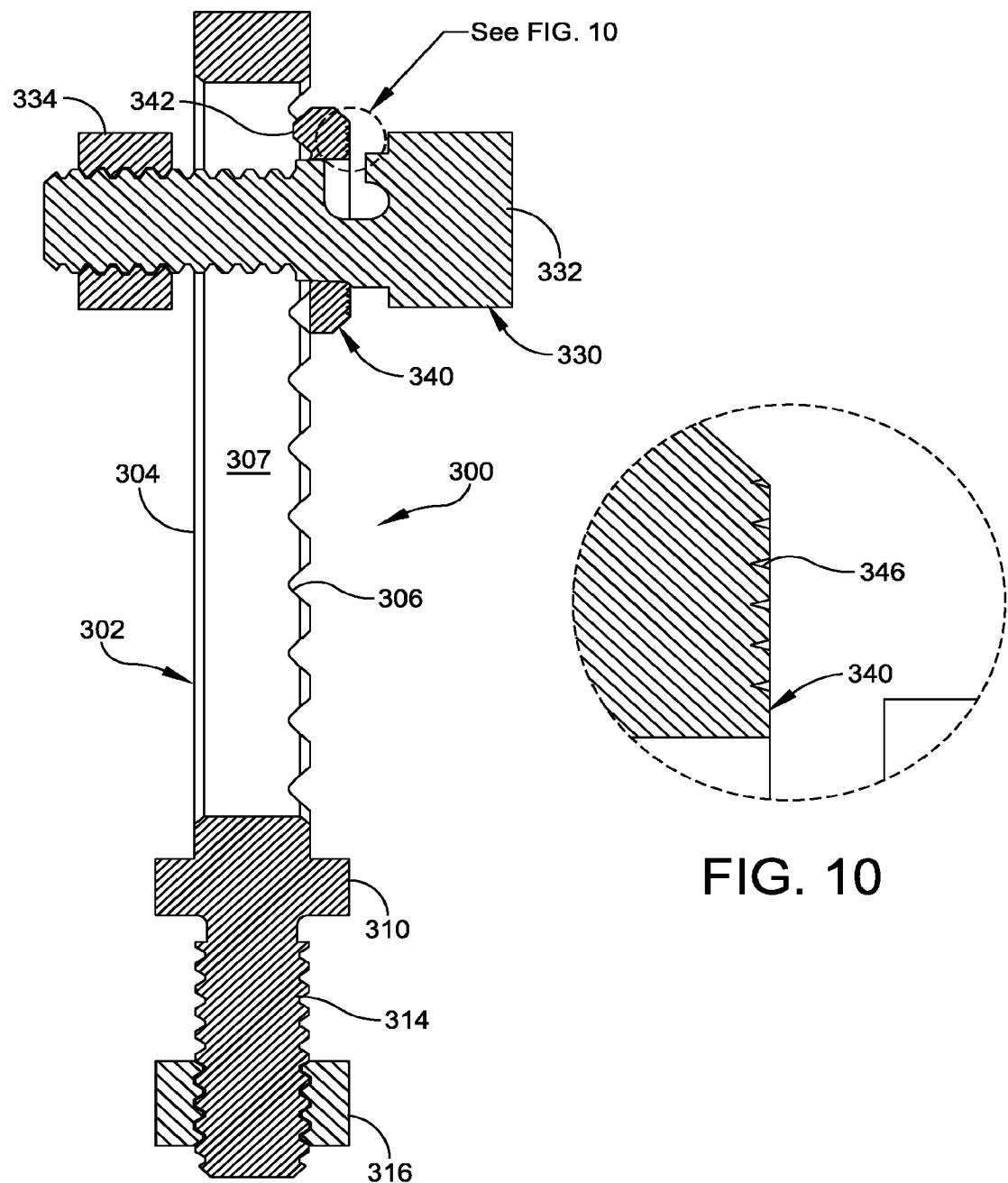
FIG. 9 is a cross sectional view taken along section line 9-9 of FIG. 8.
FIG. 10 is an enlarged detail of FIG. 9.

As shown in FIG. 7, the post 302 has a plurality of grooves 306 on at least one side face of the post, oriented perpendicular to the length (longitudinal axis) of the post. In some embodiments the opposite side surface 304 of the post 302 is flat, as shown in FIG. 8. In other embodiments, both side faces of the post have grooves 306. The washer 340 includes a ridge 342 adapted to engage one of the grooves 306. This prevents the bolt 330 from slipping relative to the post 302, particular when a component of the force applied to the bolt 330 is parallel to the direction of the slot 307 of the post 302. In some embodiments, the washer 340 is of the same type described above, and the ridge 342 is included on the face of the washer opposite the textured gripping surface 346.

In some embodiments, the surgeon can also insert rods 350 into the bone using the circulator fixator 100. A pin cube 351 (FIG. 1C) can be mounted in the slot (e.g., 154, FIG. 1C) for fixing the pin 350 (also referred to as a rod).

Figure 33:
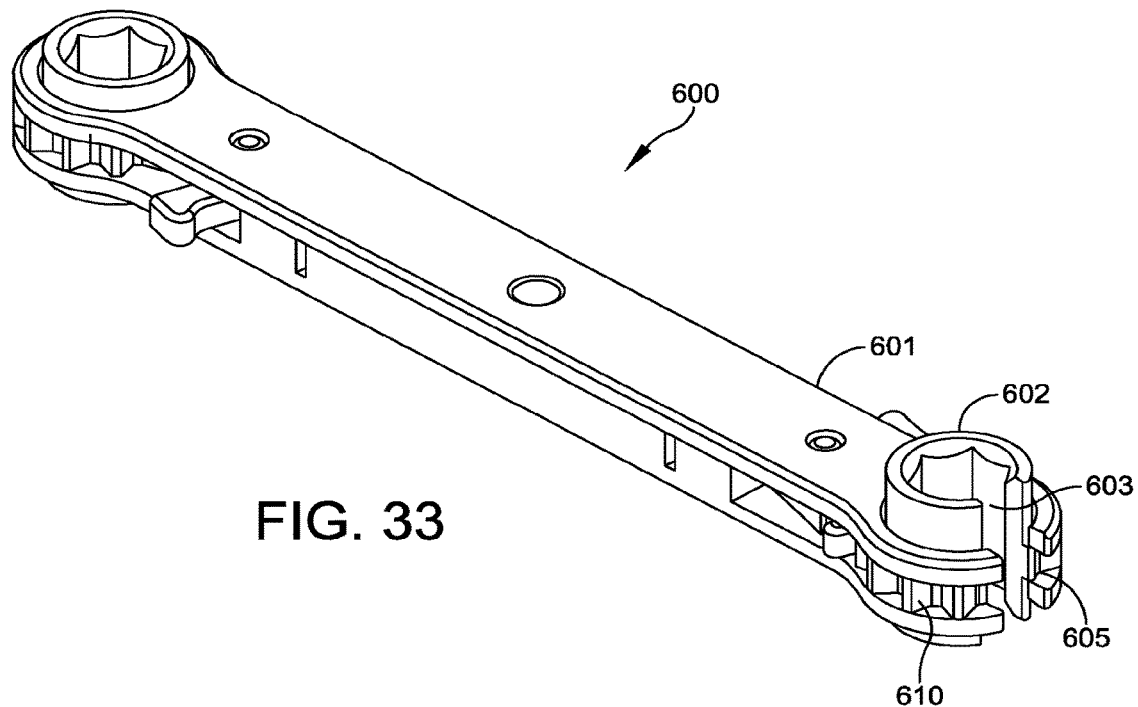
FIGS. 33 and 34 are isometric and plan views of a wrench used to tighten the fixation elements and pin of FIG. 1C.
Figure 34:
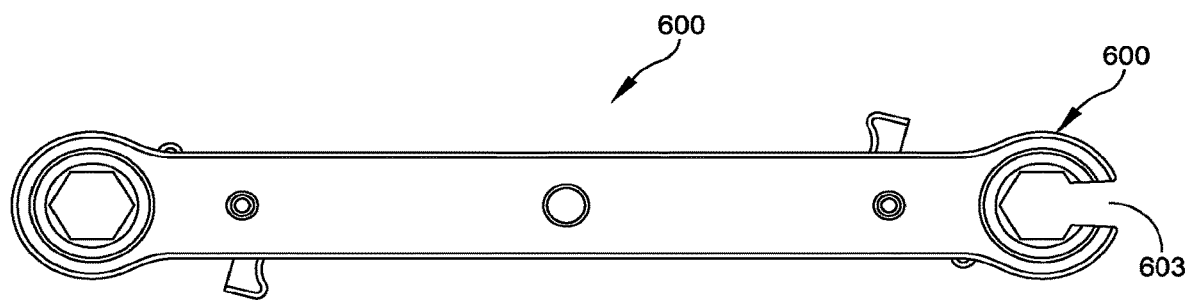
Figure 35:
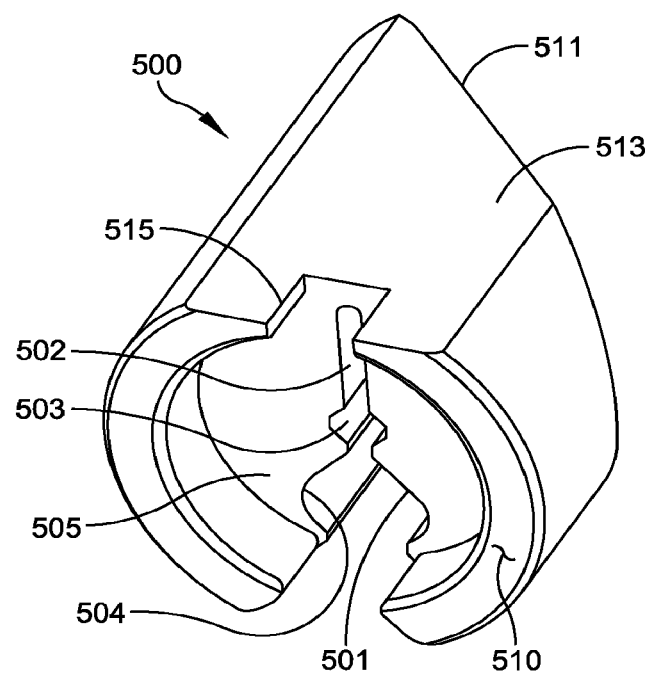
FIGS. 35 and 36 are front and rear isometric views of a clip for securing a sponge to one of the wires or rods of FIG. 1C.
Figure 36:
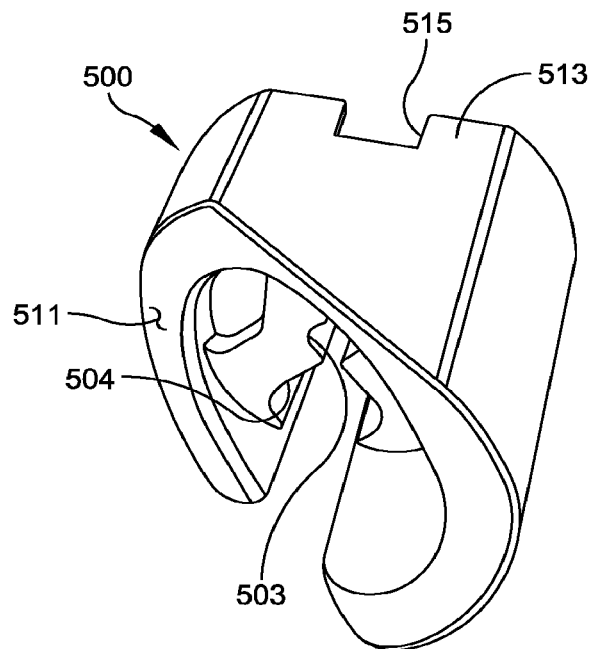
Figure 37:
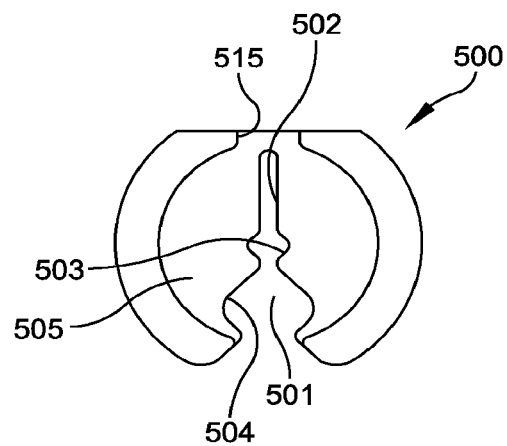
FIG. 37 is a front end view of the clip of FIG. 35.
Figure 38:
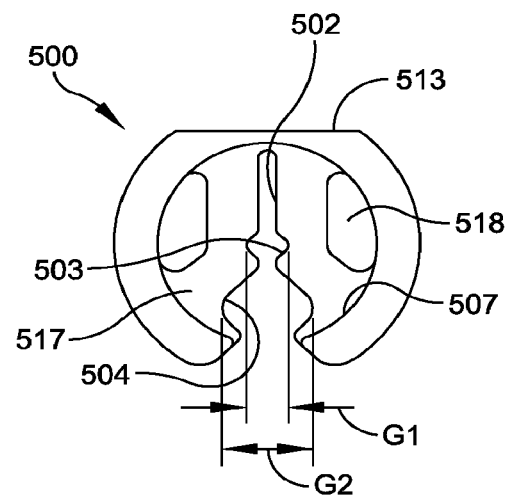
FIG. 38 is a rear end view of the clip shown in FIG. 36.
Figure 39:
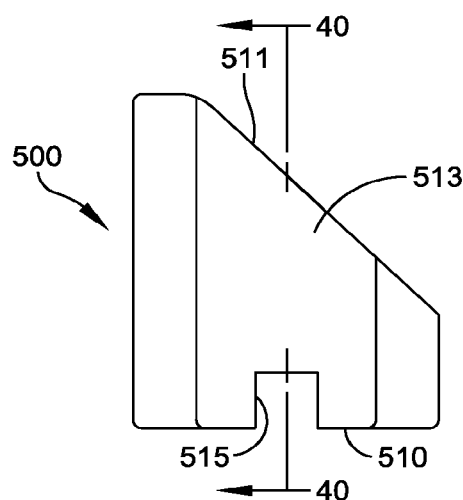
FIG. 39 is a top plan view of the clip shown in FIG. 35.
Figure 40:
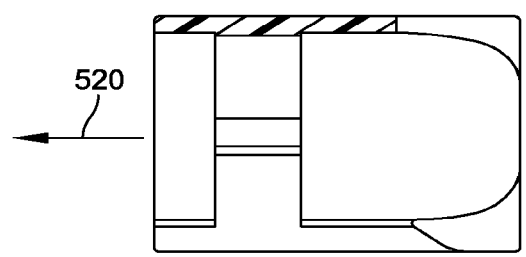
FIG. 40 is a cross sectional view taken along section line 40-40 of FIG. 39.

In some embodiments, the surgeon tightens the bolts 330 using a ratcheting wrench 600 (FIGS. 33 and 34) having an open socket that can slide over a threaded rod to tighten or loosen a bolt or nut. The wrench has a ratchet mechanism. In some embodiments, the ratchet mechanism includes a switch pin biased against a gear 610 by a spring to act as a pawl, to allow rotation in one direction. The wrench body 601 has an open end 605, and the rotating socket 602 has an open end 603. To place the wrench in position on the rod, the open end 603 of the socket is aligned with the open end 605 of the wrench body, as shown in FIGS. 33 and 34. This wrench configuration is particularly useful for tightening or loosening threaded rod, bolts and nuts.

In other embodiments (not shown), the switch pin is omitted. The direction of rotation of the wrench is fixed for applying torque only when rotated in one direction. A spring-biased piston with a beveled piston surface acts as a pawl that engages the gear 610 of the hexagonal socket 602 to allow one-way rotation of the hexagonal socket. The wrench 600 is oriented with one side facing upwards to apply torque for tightening bolts 330, and with the other side facing upwards to apply torque for loosening the bolts. In some embodiments, indicia are placed on the wrench, so the user can quickly determine which side of the wrench should face upwards for any given tightening or loosening step.

Figure 31:
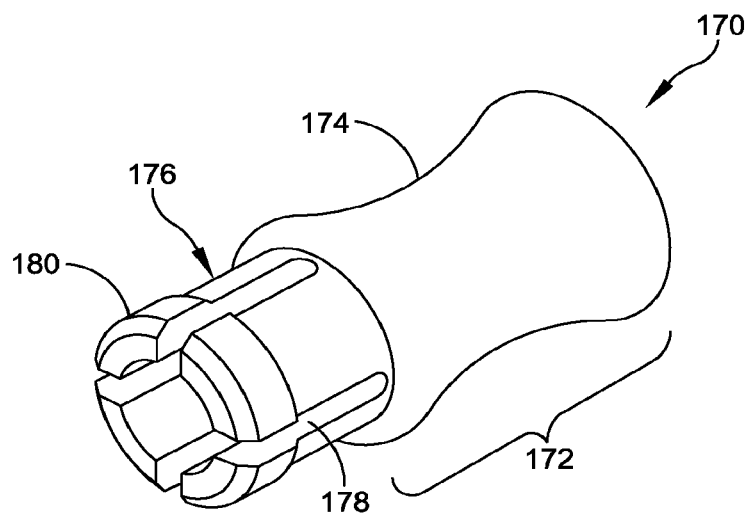
FIG. 31 is an isometric view of the plug shown in FIG. 1B.
Figure 32:
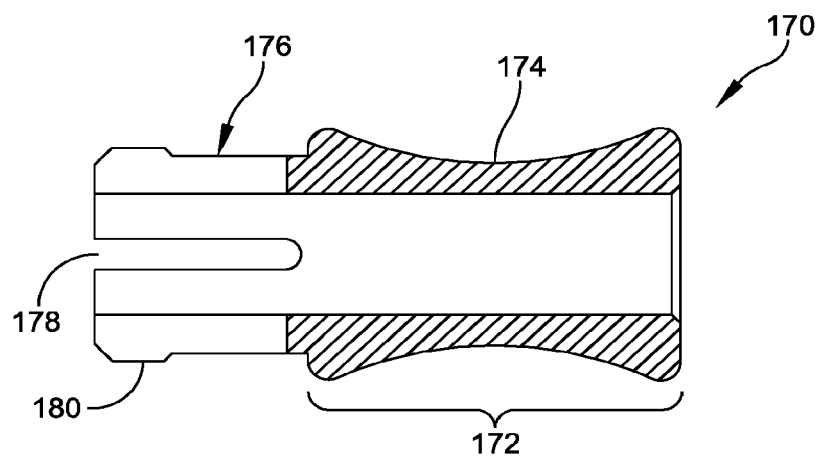
FIG. 32 is a cross sectional view of the plug of FIG. 31.

In some embodiments, as shown in FIGS. 31 and 32, the device further comprises a plurality of detachable plugs 170. Each plug 170 has a shape and size adapted to be detachably retained in a respective one of the openings (e.g., 114a), for retaining the bolt 330 in the slot 110 prior to tightening the nut 334 and bolt 330. Each plug 170 has a compressible tubular end 176 and a ridge 180 for retaining the plug within a respective one of the openings 114a. The scrub technician can quickly and easily insert one of these plugs in each opening 114a, 114b of a slot 110 for retaining pre-assembled, pre-loaded fixation devices 330, posts 300, or pin cubes on the circular fixator.

In some embodiments, the plug 170 includes a gripping portion 172, which may include a gripping surface 174, such as a contoured portion. The plug 170 further includes a plug portion 176, which is shaped to fit the openings (e.g., 114a, 114b) at the end of each slot. For a circular opening (e.g., 114a), the plug portion 176 is generally shaped as a circular cylinder. The plug portion 176 further includes a plurality of slots 178 oriented in the longitudinal direction. For example, the plug portion 176 may have four slots evenly spaced about the circumference of the plug portion 176. The plug portion 176 further includes a ridge 180 for retaining the plug 170 in the opening 114a. The ridge is greater in diameter than the opening 114a. The slots 178 permit the members of the plug portion 176 to be squeezed together for insertion into, or removal from, the openings. The plug is made of a plastic materials such as acrylonitrile-butadiene-styrene (ABS).

In some embodiments, a plurality of leg positioners hold the patient's leg in a neutral position while the surgeon inserts wires and/or rods in the leg. The leg positioners generally include at least one Y-shaped member (or round or curved member) having a concave or angled portion for supporting a limb of a patient, and a mounting device for attaching the positioner to one of the plurality of rings without a tool.

Figure 11A:
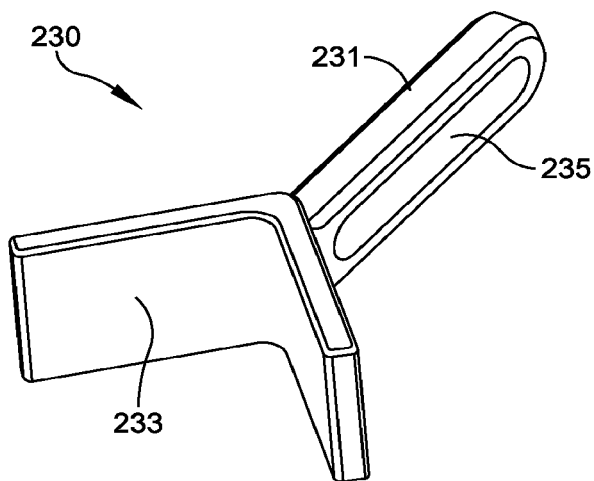
FIGS. 11A and 11B are isometric and plan views of a medial-lateral foot support shown in FIG. 1A.
Figure 11B:
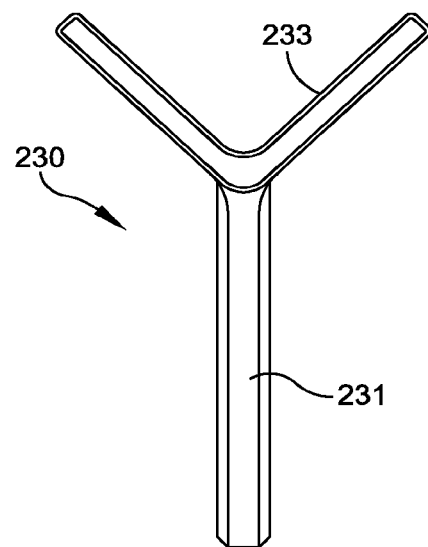

FIGS. 1 and 11A-11B show an example of a medial-lateral leg positioner 230, in which the Y-shaped member 230 includes a support arm 231 having a slot 235 through the arm. An angled support member 233 is attached to the arm 231. The leg positioner 230 can be attached to or detached from the ring 102 without using any tool.

Figure 12A:
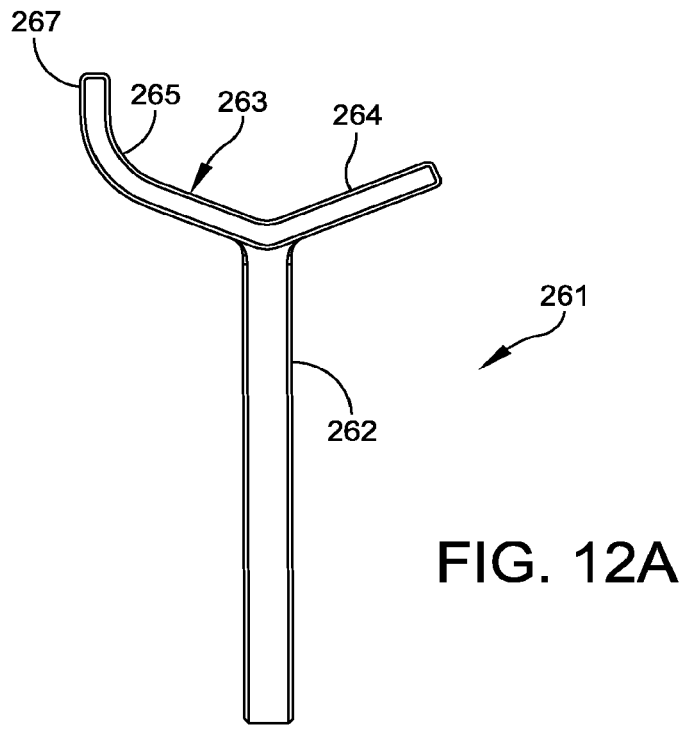
FIGS. 12A and 12B are plan and side views of another embodiment of a medial-lateral foot support suitable for use with the circular fixator of FIG. 1A.
Figure 12B:
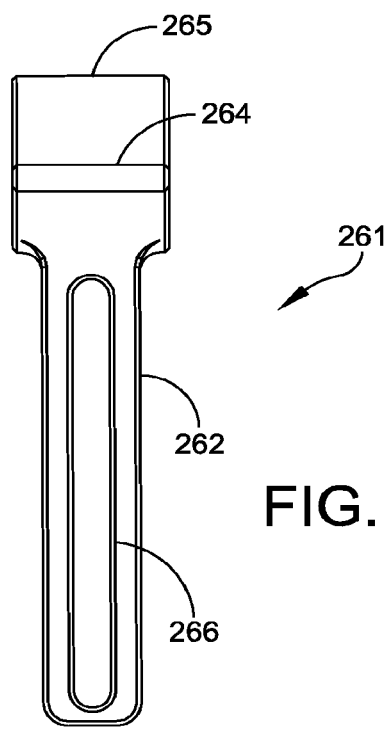

FIGS. 12A and 12B show another example of a medial-lateral leg positioner 261, having a support arm 262 and a support member 263. The support member 263 is asymmetrical, and includes an extended cup-shaped member 265 configured to extend under and support the foot. The extended member 265 can be curved or angled. In some embodiments, the extended member 265 ends in a substantially flat portion 267. The other portion 264 of the support member 263 can be flat or curved, and can be similar to the member 233 in FIG. 11A. The support arm 262 has a slot 2266 through the arm. The leg positioner 230 can be attached to or detached from the ring 102 without using any tool.

Figure 13:
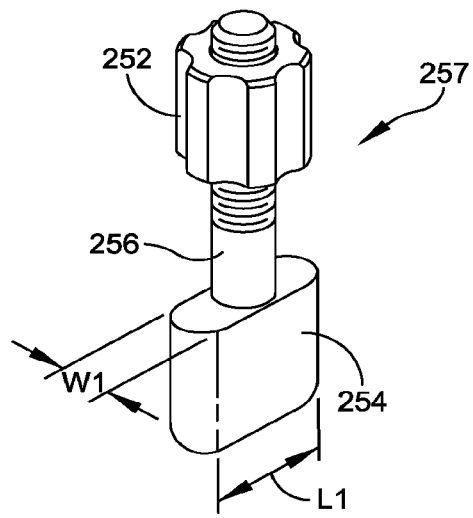
FIG. 13 is an isometric view of a mounting device for the foot support shown in FIG. 11.

In some embodiments, the leg positioner 230 is attached to the ring 102 by a mounting device 257 (FIG. 13) comprising a threaded member 256 adapted to fit through the slot (e.g., 110) of one of the plurality of rings 102 and through the slot 235 of the support arm 231 simultaneously, for attaching the arm 231 to the ring 102. The threaded member 256 has a head 254 at one end. The head 254 has a width W1 smaller than a width of the slots 110 of the rings, and a length L1 greater than the width of the slots 110 of the ring 102. The length is selected so that the head can engage one of the curved arcs of the scallop-shaped recesses 112a, 112b on each side of a slot 110 of one of the plurality of rings 102.

In some embodiments, the mounting device 257 further includes a threaded knob 252 configured so that it can optionally be received in one of the curved arcs of the scallop-shaped recess 112a of the one of the plurality of rings 102 (although the knob 252 can be located in other positions. The threaded knob 252 is configured for receiving the threaded member 256 of the mounting device 257. The threaded knob 252 has a size that is greater than a width of the slots 110 of the rings, but smaller than the dimension of the openings 114a, 114b. Thus, the mounting device can be pre-assembled to the Y-shaped member 230, and the knob can then be passed through the opening 114a, 114b to install the leg positioner 230 on the ring 102. Alternatively, the pre-assembled mounting device 257 can be installed on the ring by orienting the head 254 parallel to the slot 110, and passing the head 254 through the slot 110.

Figure 14:
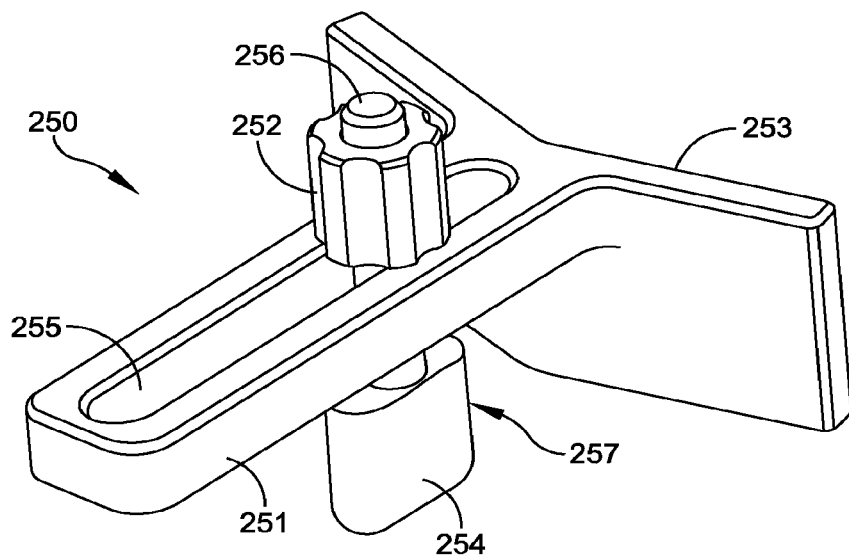
FIG. 14 is an isometric view of a medial-lateral leg support shown in FIG. 1A.

FIG. 14 shows another leg positioner 250 suitable for attachment to the top ring 142, in which the Y-shaped member 250 includes a support arm 251 having a slot 255 through the arm. An angled support member 253 is attached to the arm 251. The leg positioner 250 can be attached to the ring 142 using the same type of mounting device 257 described above (and shown in FIG. 13), and for brevity, a description of the mounting device is not repeated. The threaded member 256 of mounting device 257 is adapted to fit through the slot (e.g., 110) of one of the plurality of rings 102 and through the slot 255 of the support arm 251 simultaneously, for attaching the arm 251 to the ring 130 or 142.

These are just two examples of the leg positioner. In other embodiments, the support member 233 and/or 253 can have a different angle. In other embodiments, the support member 233 and/or 253 can have a concave curved shape.

Figure 15:
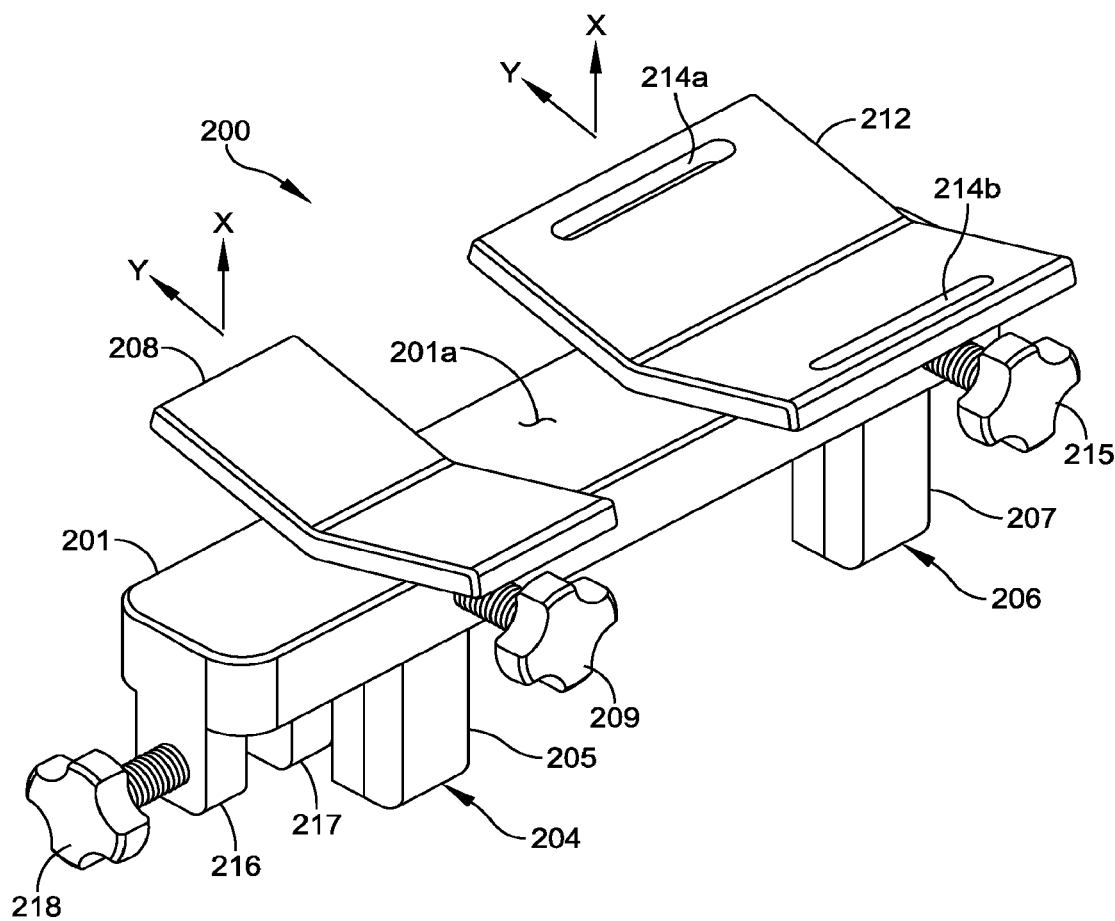
FIG. 15 is an isometric view of an anterior leg positioner shown in FIG. 1A.
Figure 16A:
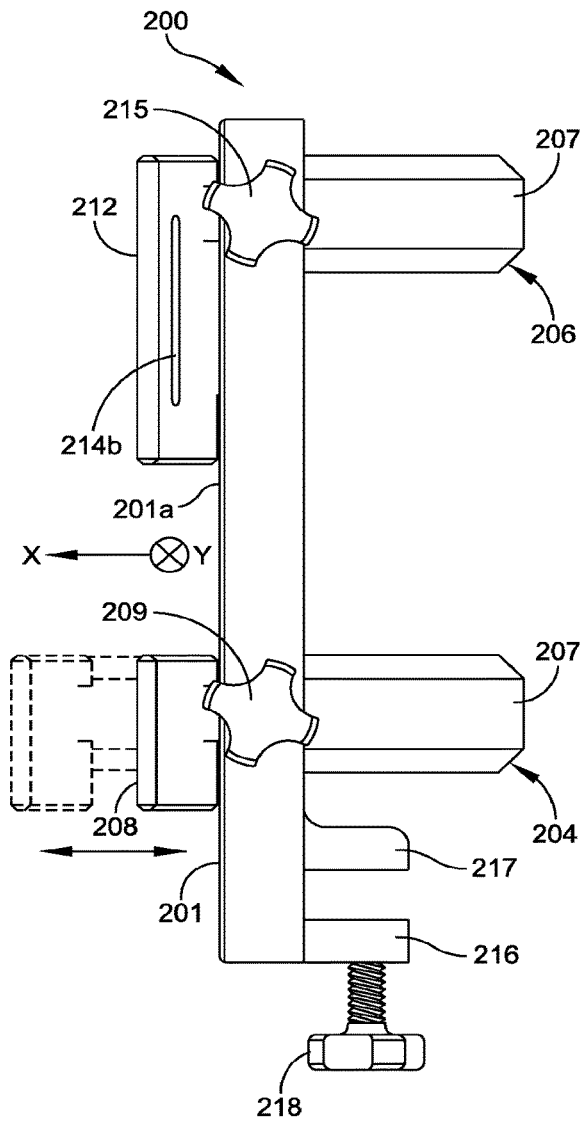
FIGS. 16A and 16B are left and right side elevation views of the leg positioner shown in FIG. 15.
Figure 16B:
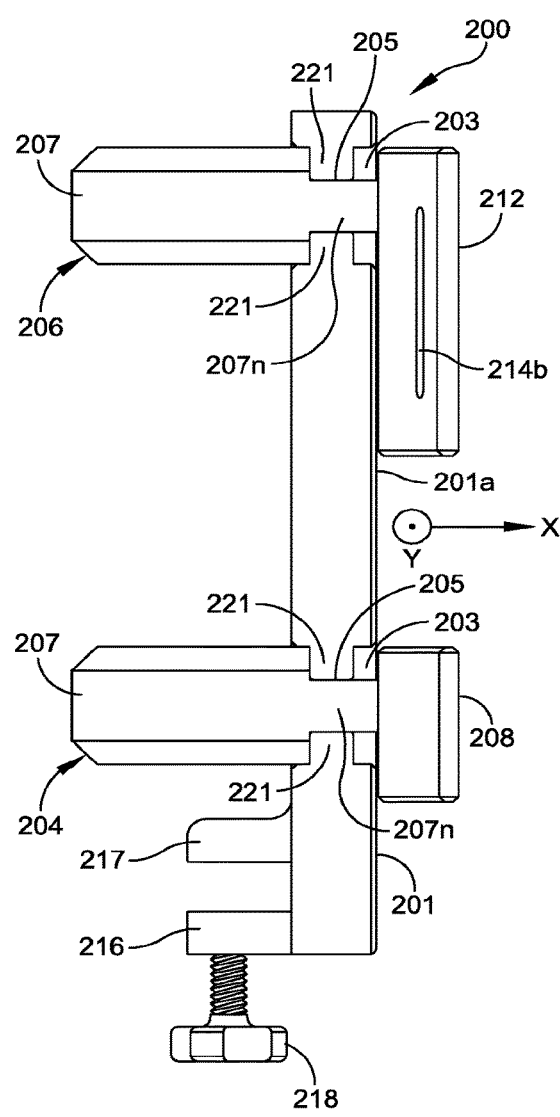
Figure 17:
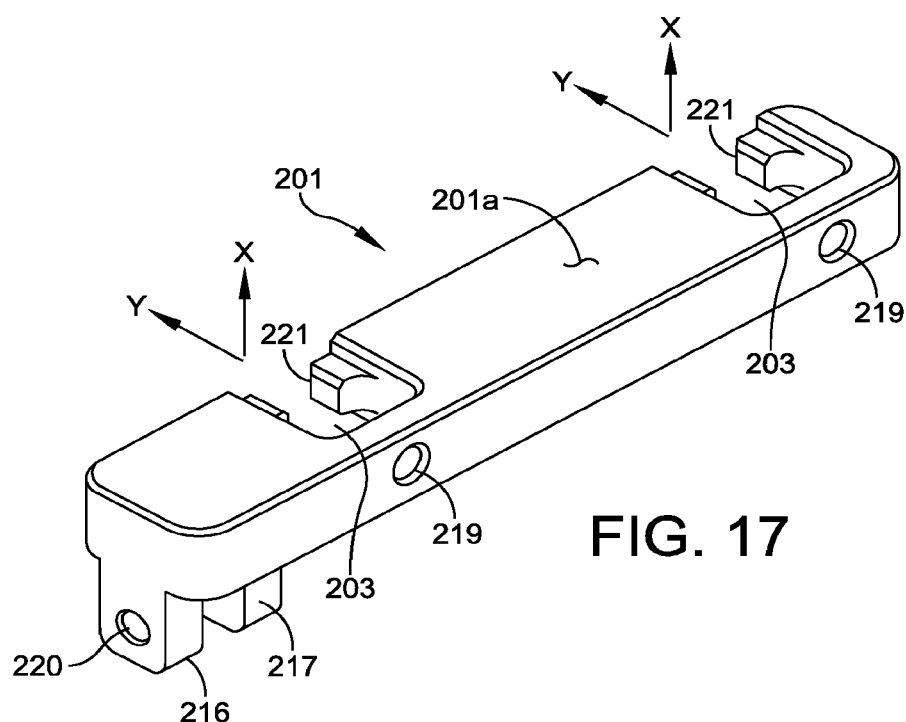
FIGS. 17-19 are isometric, left side and anterior elevation views of the positioner body shown in FIG. 15.
Figure 18:
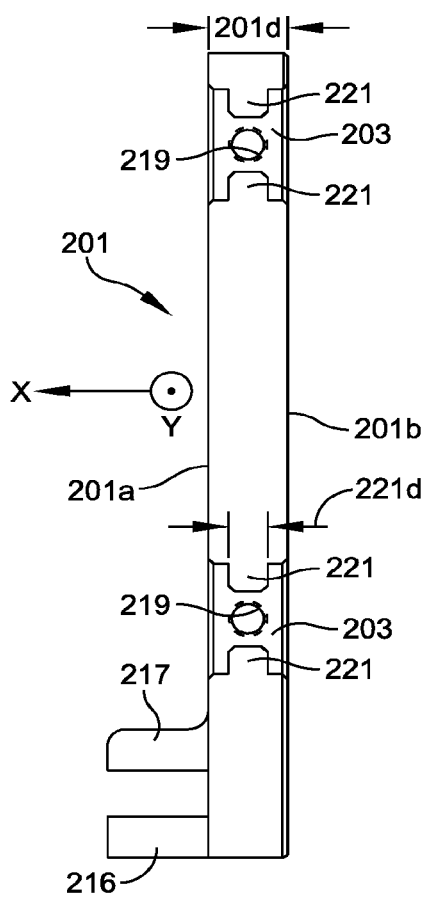
Figure 19:
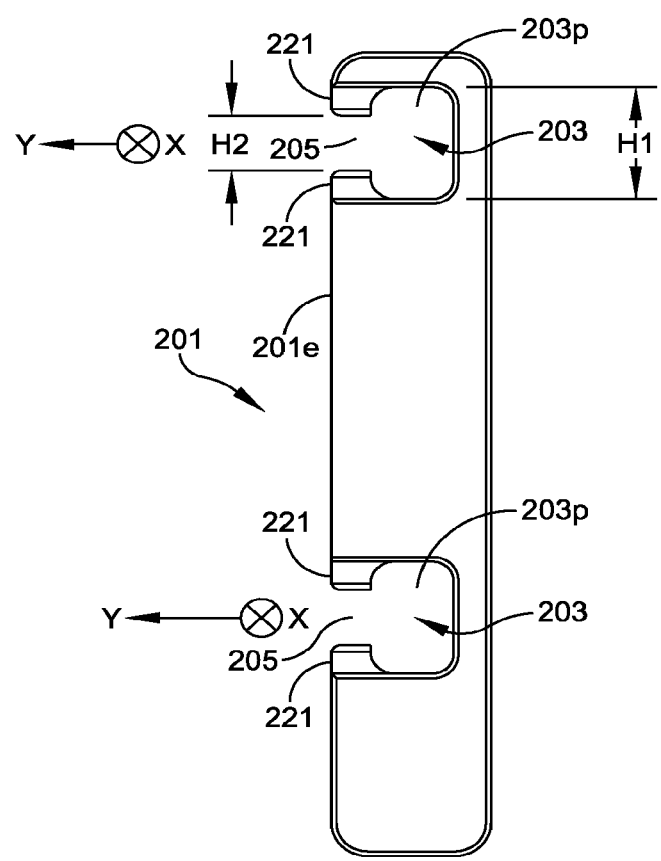
Figure 20:
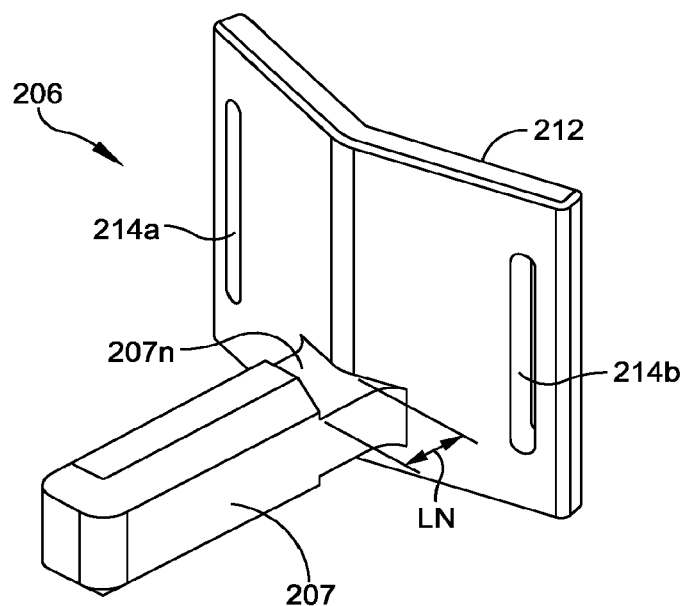
FIGS. 20 and 21 are isometric and posterior elevation views of one of the support devices shown in FIG.
Figure 21:
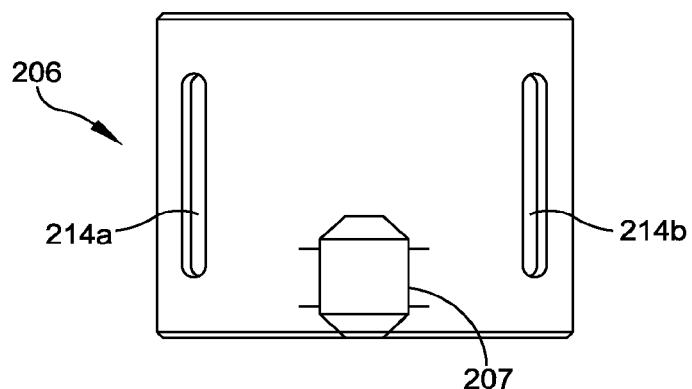

FIGS. 15-21 show another type of leg positioner 200 suitable for supporting two different portions of the leg at two different heights simultaneously. FIGS. 15, 16A and 16B are isometric, right side, and left side elevation views, respectively, of the leg positioner assembly 200. FIGS. 17-19 are isometric, side elevation and front elevation views of the body 201 of the assembly 200. FIGS. 20 and 21 are isometric and rear elevation views of the top leg positioner 212 of FIG. 15.

Leg positioner 200 includes a plurality of independently positionable support devices 204, 206 for supporting a limb of a patient. Support device 204 has a respective arm 207 and a respective concave or angled portion 208 attached to the arm 207, for supporting the heel. Support device 206 has a respective arm 207 and a respective concave or angled portion 212 attached to the arm 207, for supporting the calf. The positions of the support devices 204, 206 can be switched by the surgeon or technician, if desired.

Leg positioner 200 includes a body 201 having a plurality of openings 203 for slidably receiving respective ones of the plurality of support devices 204, 206 through the openings 203. In some embodiments, the support devices 204, 206 are of the same type as each other. In some embodiments, the support devices 204, 206 are of different types from each other (i.e., include different concave or angled portions). In other embodiments, the support devices 204, 206 are of different sizes and/or different types.

In some embodiments, the concave or angled portion 212 of at least one of the support devices 206 has a plurality of slots 214a, 214b for receiving a retaining strap (not shown) therethrough. For example, the technician or surgeon can optionally run a Velcro strap through the slots 214a, 214b and wrap the strap around the patient's leg.

The leg positioner 200 also includes a respective retaining device 209, 215 proximate each respective openings 203, for retaining a respective one of the support devices 204, 206 in a continuously selectable position.

The leg positioner 200 further includes a mounting device 218 for detachably mounting the leg positioner to an edge of one of the plurality of rings. For example, as shown in FIG. 1A, the leg positioner 200 can be attached to the bottom ring 102.

As best seen in FIGS. 17-19, the body 201 has a first opening 203. The first opening 203 includes a passage 203p (FIG. 19) penetrating completely through the body 201 from a first face 201a of the body 201 to a second face 201b opposite the first face, and a relatively narrow slot 205 extending from the passage 203p to a side edge 201e of the body. The slot 205 has a height H2 that is less than a height H1 of the first opening 203.

As shown in FIGS. 15, 16A, 20 and 21, each support device (also referred to as a leg positioning element) 204 (206) comprises an arm 207 adapted to slidably fit in the first opening 203 for sliding along a first direction X normal to the first face 201a. A support 208 (212) is adapted to support a first portion of a limb of a patient. A neck portion 207n connects the support 208 (212) to an end of the arm 207. The neck portion 207n is adapted to slidably fit in the slot 205, to permit removal of the leg positioning element 204 (206) from the body 201 through the slot 205 in a second direction Y parallel to the first face 201a. When the support device 204, 206 is advanced in the X direction, so the retaining members 221 engage the arm 207, the support device 204, 206 is constrained from moving in the Y direction.

Referring now to FIG. 16B, the body 201 has a first and second retaining members 221 defining the slot 205 therebetween. The retaining members 221 have a depth 221d in the first direction (X) that is less than a depth 201d of the body 201 in the first direction. The length of the neck portion 207n is greater than the depth 221d of the retaining members 221, and is sufficiently long so that the end of the arm 207 can be backed out (in the −X direction) until the neck 207n is aligned between the retaining members 221, and can be moved in the Y direction through the retaining members 221. In some embodiments, the neck portion 207n has a length LN (FIG. 20) that is less than the depth 201d of the body 201 in the first direction X. FIG. 16B shows the positioner 200 with both support devices 204, 206 in the fully retracted position (wherein the concave or angled portions 208, 212 abut the first face 201a of the body 201. In this position, the neck portions 207n are positioned between the retaining members 221, to permit the support devices 204, 206 to be removed from the body by sliding the support devices in the Y direction, through the slot 205 between the retaining members 221. Conversely, when the arms 207 are extended so the concave or angled portions 208, 212 do not abut the first face 201a of the body 201, the arms 207 can slide in the X direction, but cannot move in the Y direction.

In some embodiments, when the surgeon completes insertion of wires and/or pins, the leg positioner assembly 200 can be removed easily by fully retracting each of the support devices 204, 206, and sliding the support devices in the Y direction relative to the body 201 of the leg positioner assembly 200 (or sliding the body 201 relative to the support devices 204, 206). Thus, the leg positioner assembly 200 can be removed without disturbing the position of the leg relative to the frame 100.

The leg positioner 200 further includes a first locking device 209 (215) for locking the arm 207 in a fixed position relative to the body 201 without using a tool. For example, as shown in FIG. 15, the locking device 209 (215) can be a screw including an enlarged head for gripping and advancing the screw without a tool.

Some embodiments further comprise a mounting device 218 for mounting the body to the circular fixator 100 without using a tool. For example, body 201 has two jaws 216, 217 spaced sufficiently far apart to receive an edge of one of the rings 102, and a screw 218 which penetrates the bottom jaw 216.

Figure 22:
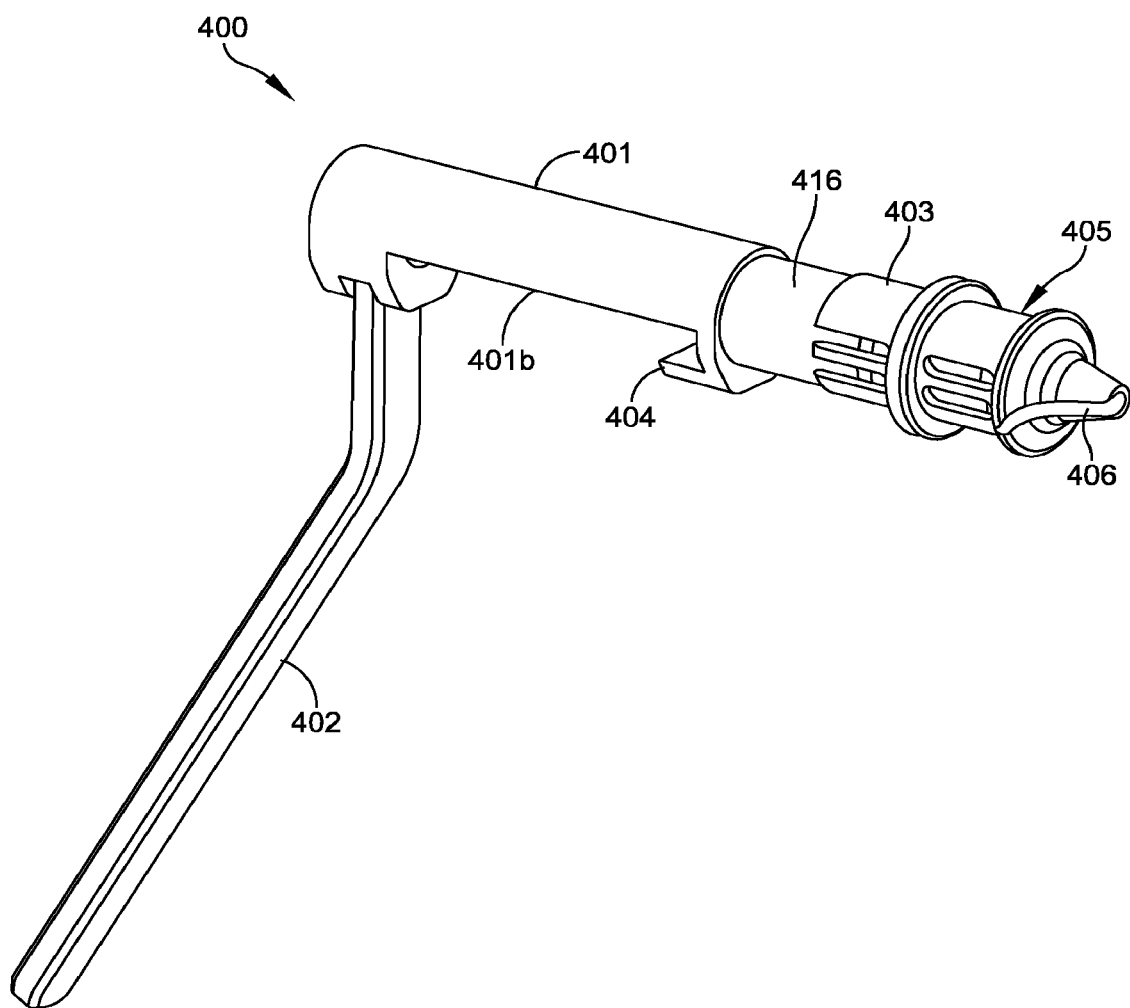
FIG. 22 is an isometric view of a wire drill guide for inserting the wires shown in FIG. 1C, with the tip extended.
Figure 23:
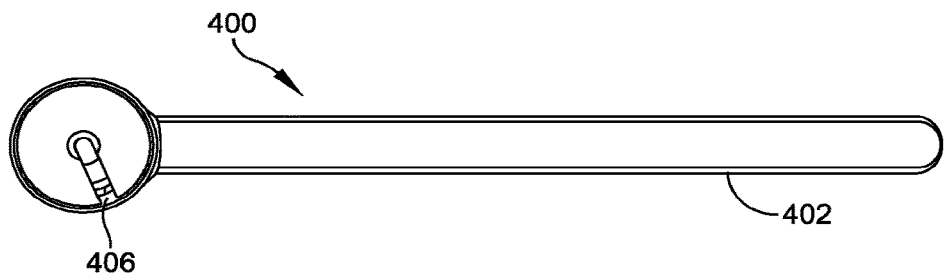
FIGS. 23-25 are front, side and top plan views of the wire drill guide shown in FIG. 22.
Figure 24:
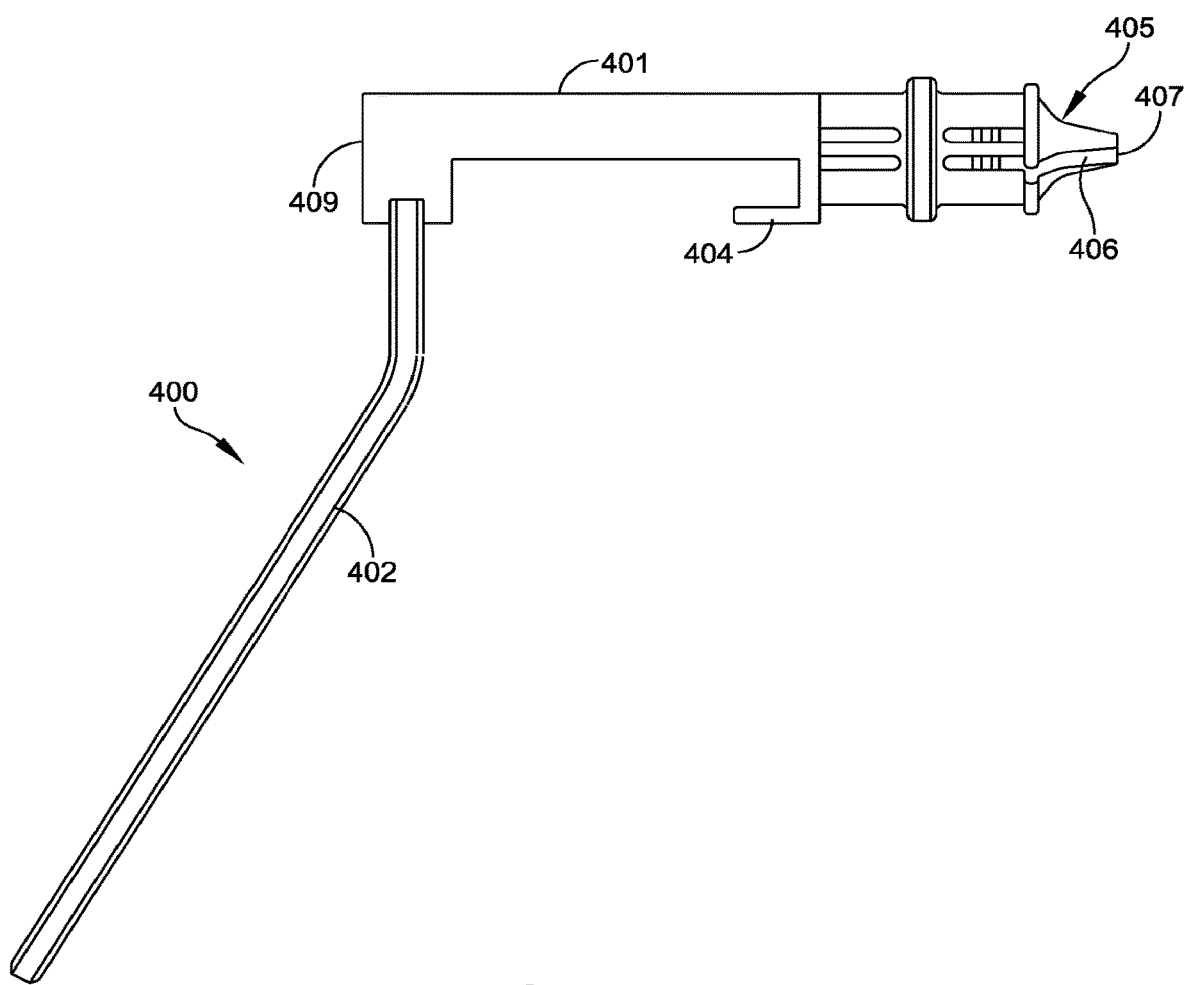
Figure 25:
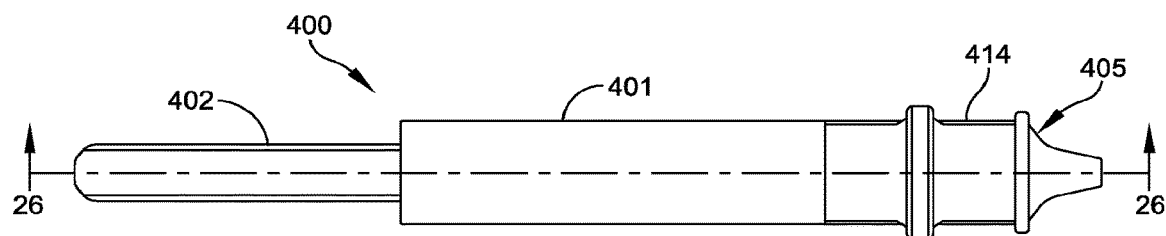
Figure 26:
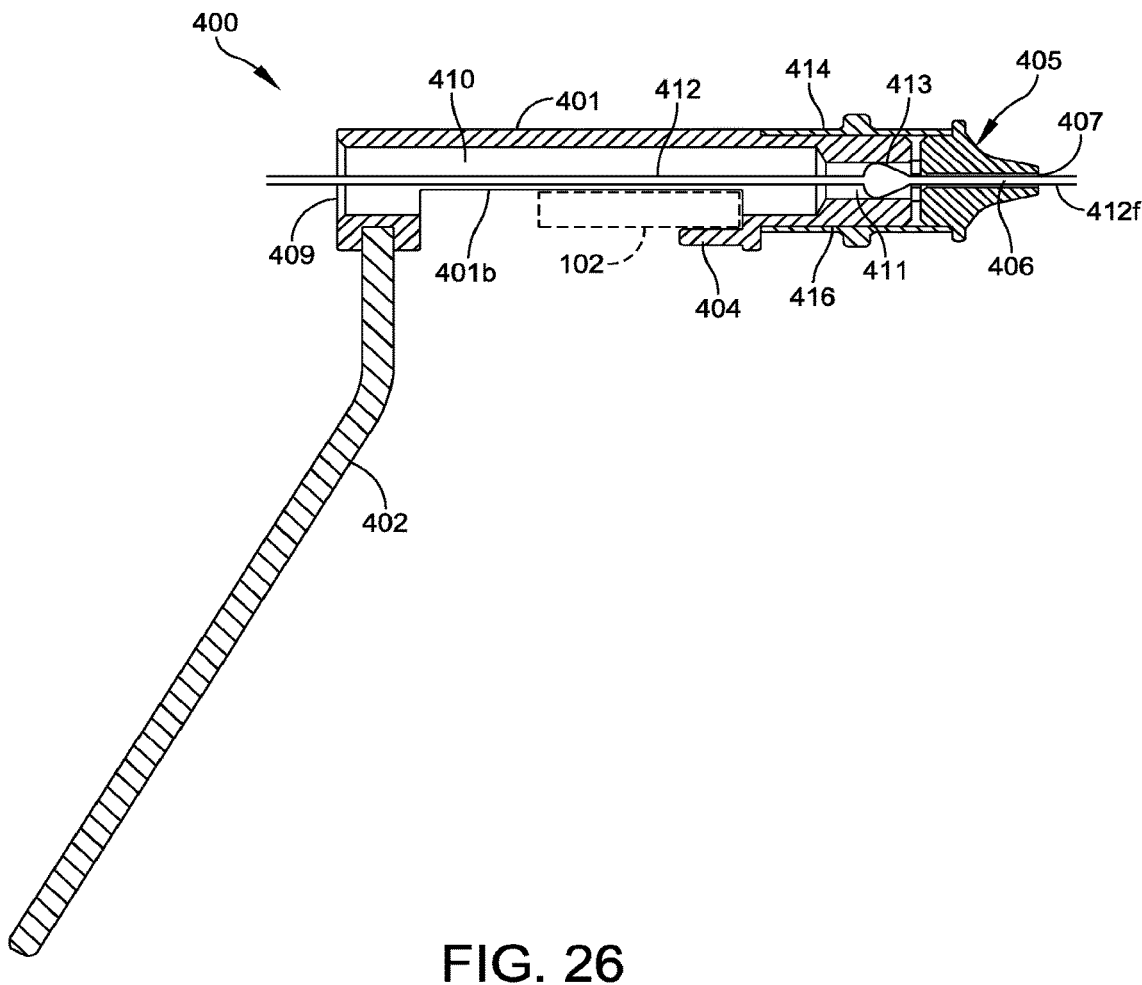
FIG. 26 is a cross sectional view taken along section line 26-26 of FIG. 25.

FIGS. 23-26 show a wire drill guide 400 for inserting wires 412 to fix the patient's leg to the frame 100. The drill guide 400 is adapted for use with both smooth wire (not shown) and olive wire 412 (having an olive structure 413). FIG. 22 is an isometric view, and FIG. 24 is a side elevation view. FIG. 23 is a front elevation view of the wire insertion tip 406 shown in FIGS. 22 and 24. FIG. 25 is a top plan view, and FIG. 26 is a cross-sectional view taken along section line 26-26 of FIG. 25. FIG. 26 includes the ring 102 of circular fixator 100 and a wire 412 having an olive structure 413 for reference. The ring 102, wire 412 and olive structure 413 are not part of the drill guide 400 but are included in FIG. 26 for ease of understanding the use of the wire drill guide 400.

The drill guide 400 includes a barrel 401, through which the wire 412 can be run. The barrel 401 is generally in the form of a hollow, half-cylindrical shell, with flat edges 401b on the bottom thereof. A handle 402 is provided at the rear end of the drill guide 400. The front end of the barrel 401 has a rearward extending finger 404. With the flat edges 401b of the barrel resting on the top or bottom surface of one of the rings 102, 130, 142, the rearward extending finger 404 wraps around under the inner edge of the ring (e.g., 102), to provide stability while the surgeon inserts the wire 412. For example, in FIG. 26, a cross-section of the ring 102 is shown in phantom. By positioning the drill guide 400 relative to the inner edge of the ring 102 as shown, the drill guide 400 is stably directed radially inward toward the patient's leg.

As shown in FIG. 26, the barrel 401 has a proximal guide portion 410 with an inlet opening 409 therein at the rear of the barrel. The opening 409 of the proximal guide portion 410 is larger in diameter than the olive structure 413. The passage 410 and inlet 409 are larger than the olive 413 of a standard olive wire 412, permitting the olive to be inserted through the inlet 409. The barrel 401 also includes an outlet passage 411 which is larger in diameter than the olive 413.

The drill guide 400 further comprises a tip 405 having a central longitudinal passage 407. The passage 407 is greater in diameter than the wire 412 (e.g., K-wire), but smaller in diameter than the olive 413. (Although an example is described herein using olive wire, the same drill guide 400 can also be used with smooth wire.) The tip 405 has a slot 406 extending in the radial direction from the passage 407 all the way to the exterior surface of the tip, as best seen in FIGS. 22 and 24. Thus, if an olive wire 412 is inserted through the barrel 401 and the outlet passage 411, and advanced until the olive 413 is within or near the tip 405, the tip 405 of the drill guide 400 can be removed by passing the slot 406 of the tip over the front portion 412f of the wire 412. The remaining portions of the drill guide 400 can then be backed off over the olive 413, and the rear portion of the wire 412 (distal from the patient) is fixed to the frame 100 by the fixation element 330. The drill guide can be made of 630 stainless steel, for example.

The method of using the drill guide 400 for inserting at least one wire 412 includes placing a drill guide 400 on a ring 102 of the circular fixator 100, so as to direct the at least one wire 412 towards a bone of the patient, where the drill guide 400 has a longitudinal opening 407 adapted to pass the at least one wire 412 therethrough (but not large enough to pass the olive 413 therethrough). The surgeon or technician holds the handle 402 to position the drill guide 400. The surgeon drives the at least one wire 412 through the longitudinal opening 407 and through the bone.

In some embodiments, the drill guide 400 has a flat surface 401b and a finger 404 for wrapping around a proximal edge of the ring 102, and the step of placing the drill guide 400 includes positioning the drill guide so that the flat surface 401b engages a top or bottom face of the ring 102. The barrel is sized to be long enough (or angled) to permit the surgeon to slide the drill guide 400 forward until the tip 405 contacts the bone for precise drilling.

In other embodiments of the method, the surgeon can position the drill guide 400 under the ring 102, so that the flat surface engages a bottom face of the ring, and the finger 404 wraps around the top surface of the ring.

In some embodiments, the drill guide 400 has a proximal guide portion 410 with an opening 409 therein, the opening of the proximal guide portion larger in diameter than the olive structure 413. The step of driving the at least one wire 412 further comprises passing the olive structure 413 through the opening 409 of the proximal guide portion 410.

In some embodiments, the drill guide 400 has a removable tip 405 with a slot 406 therein and a front opening 407 for feeding the wire 412 therethrough. The wire 412 has an olive structure 413 larger than the front opening 407. The step of driving the at least one wire 412 includes driving the wire 412 until the olive structure 413 is within or near the tip 405, and removing the tip 405 of the drill guide 400 by passing the slot 407 of the tip over the wire 412.

In some embodiments, a socket 414 (collar) receives the front end of the barrel 401 and the rear end of the tip 405. In some embodiments the socket 414 has slots to provide sufficient compliance that the socket 414 can snugly receive the front end 416 of the barrel and the rear end of the tip 405. In some embodiments, the length of the front end 416 and the length of the socket 416 are selected to provide allow the socket 414 to slide part of the length of socket forward to extend the length of the drill guide (in the position shown in FIG. 22). Alternatively, the drill guide can be included in a kit having a plurality of sockets 414 of different lengths.

Figure 27:
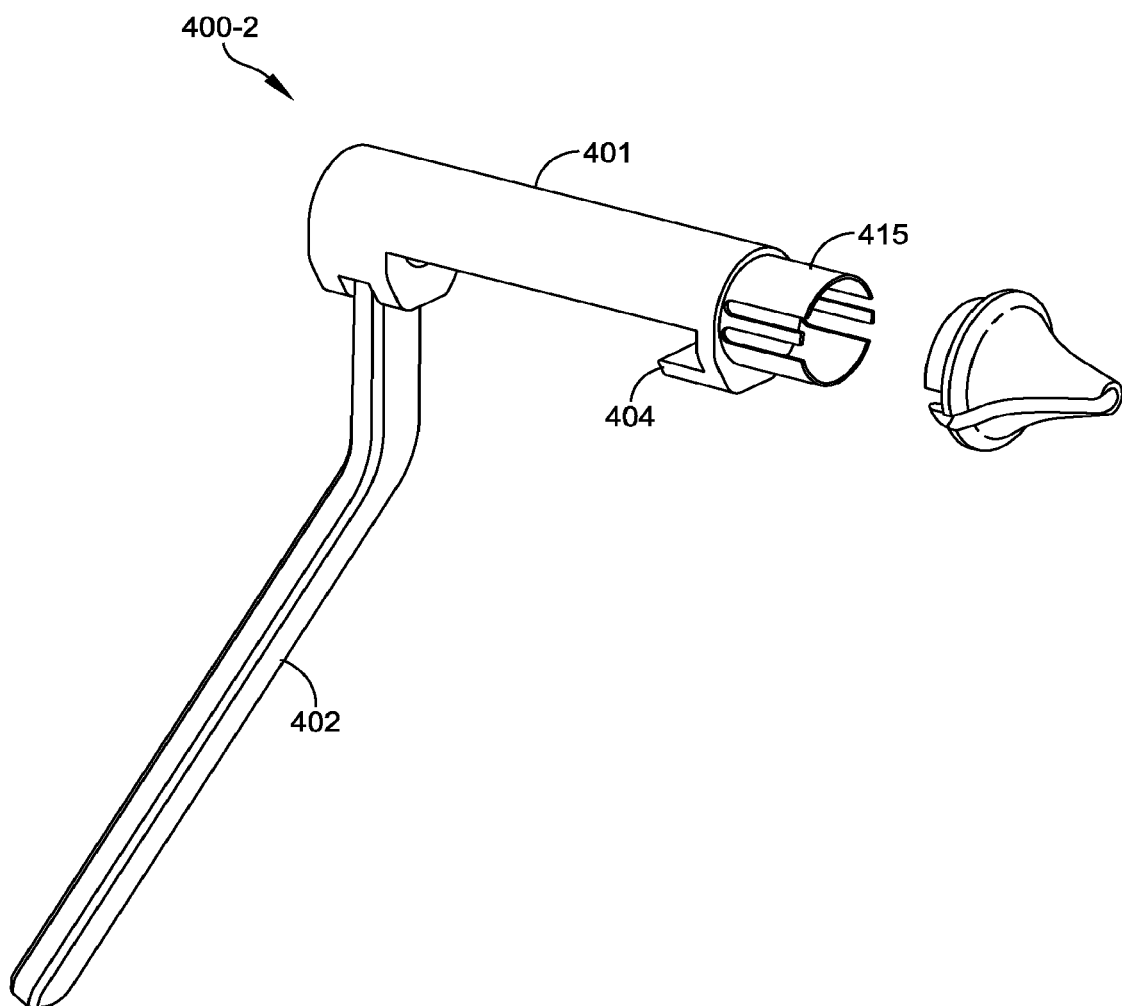
FIG. 27 is an exploded view of a second embodiment of the wire drill guide with combined tip and socket.
Figure 28:
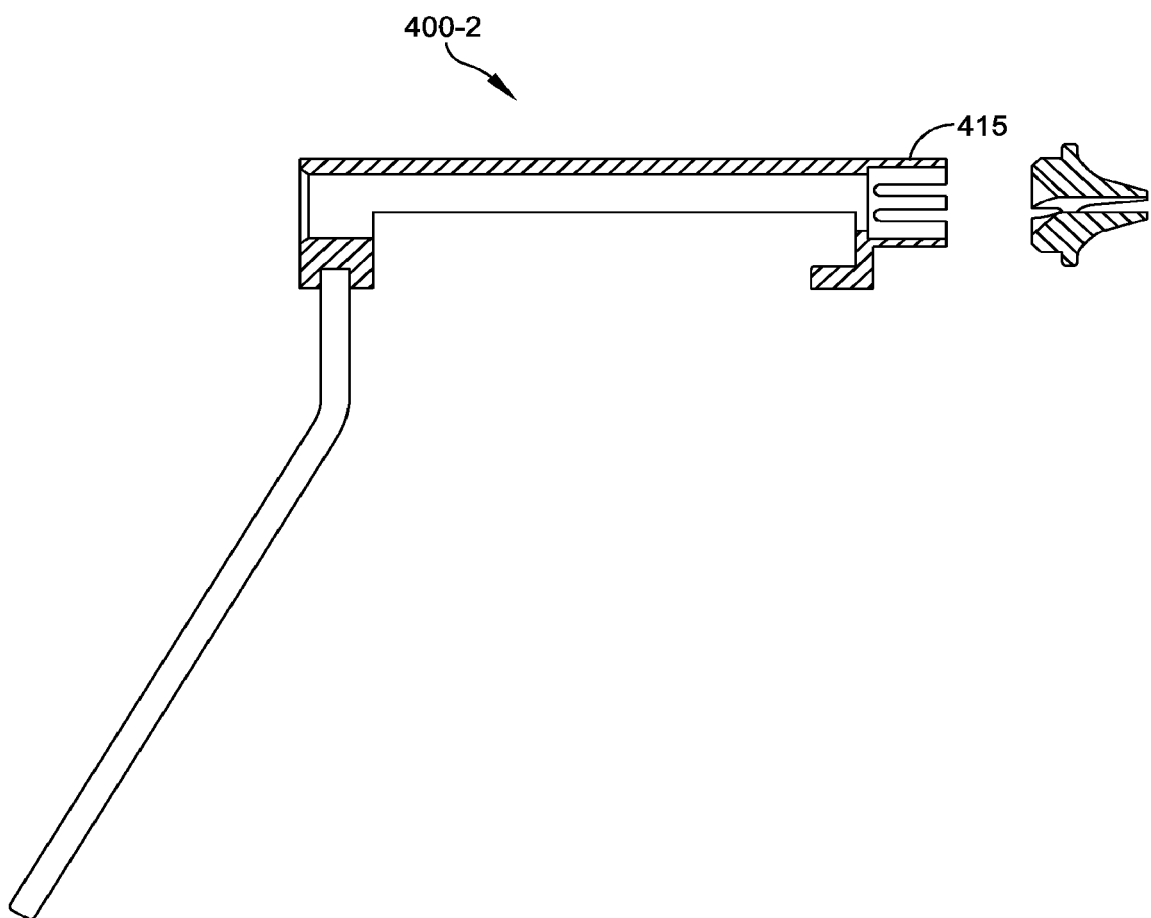
FIG. 28 is a side elevation view of the wire drill guide of FIG. 27.

FIGS. 27 and 28 are isometric and side cross sectional views of another embodiment of the drill guide 400-2, in which the barrel 401 and socket 415 are integrally combined in one unitary piece. The remaining elements of drill guide 400-2 are the same as for the drill guide 400, as indicated by like reference numerals, and descriptions of these elements are not repeated for brevity. The operation and use of the drill guide 400-2 is the same as described above with reference to FIGS. 23-26, and the description is not repeated, for brevity.

Figure 29:
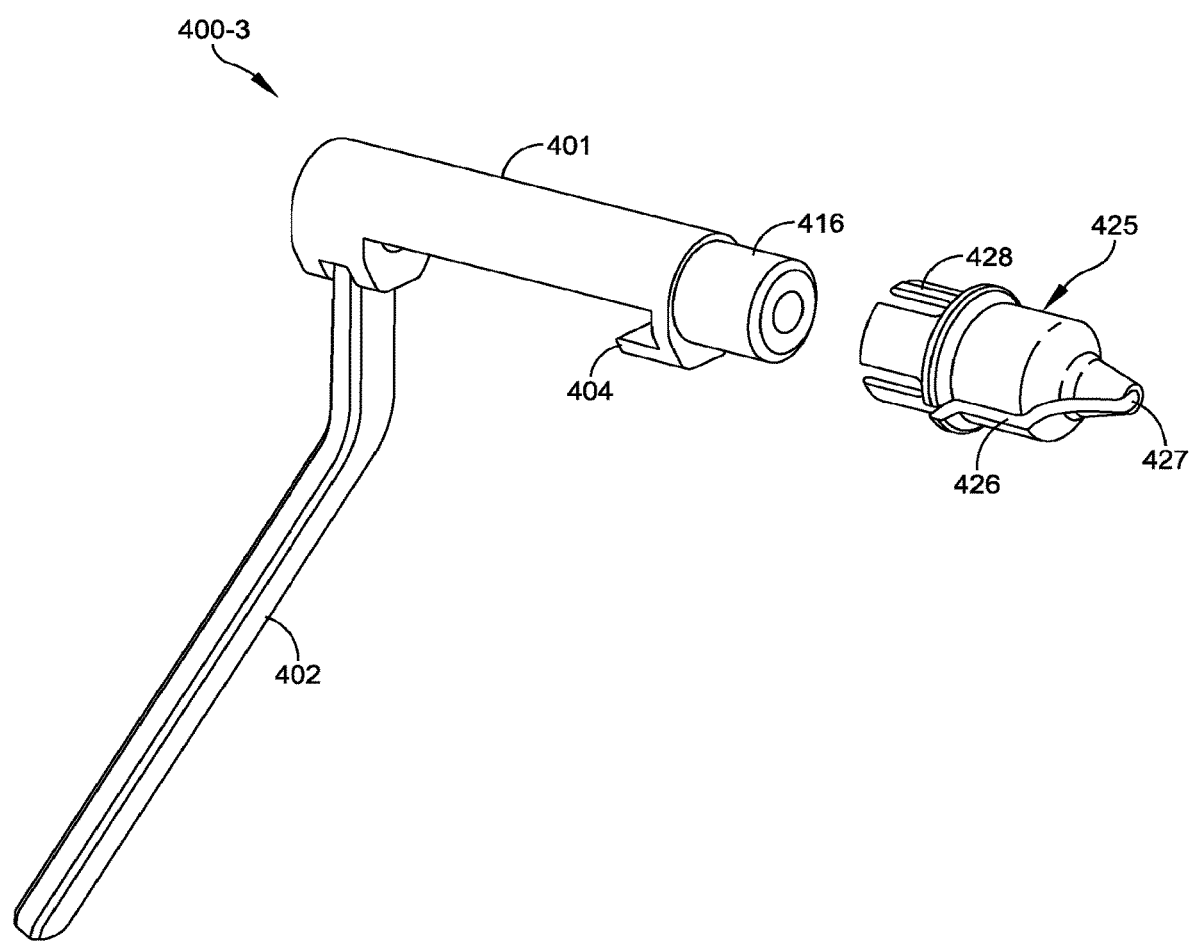
FIG. 29 is an exploded view of a third embodiment of the wire drill guide with combined barrel and socket.
Figure 30:
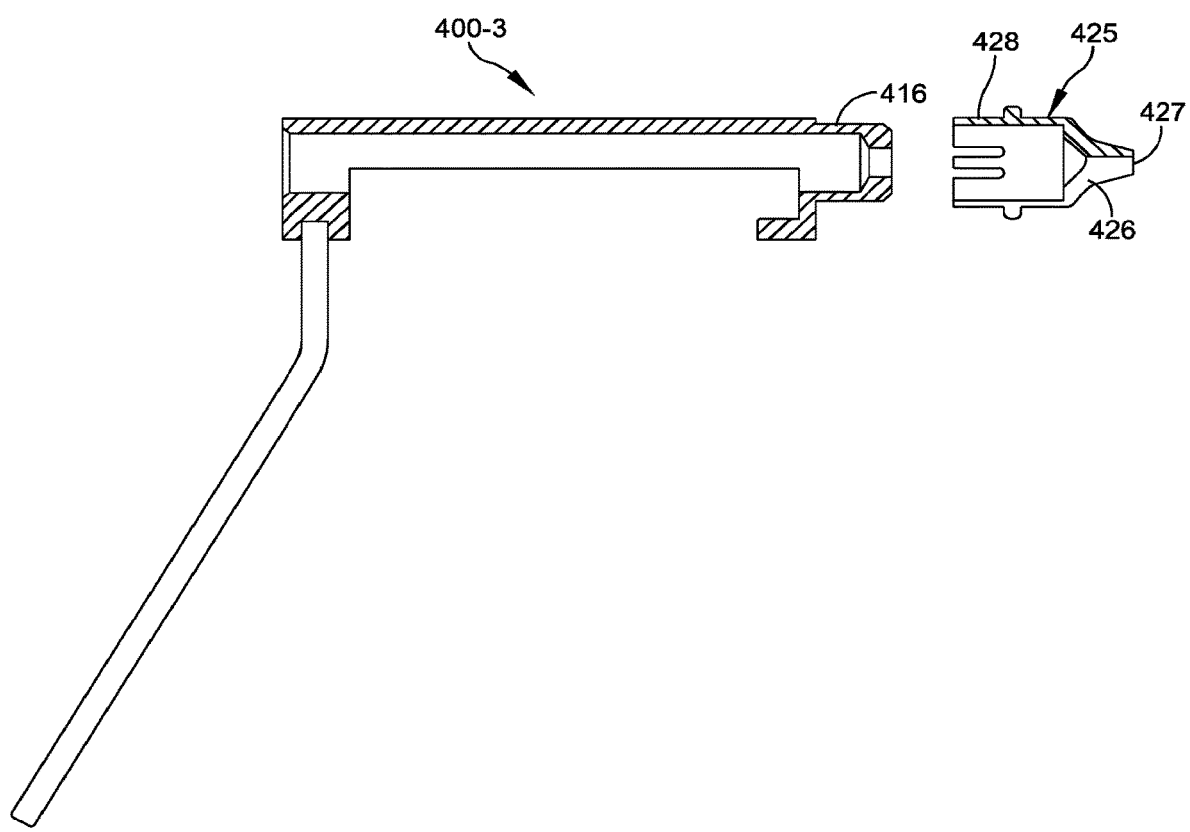
FIG. 30 is a side elevation view of the wire drill guide of FIG. 29.

FIGS. 29 and 30 are isometric and side cross sectional views of another embodiment of the drill guide 400-3, in which the tip 425 and socket 427 are integrally combined in one unitary piece. The tip 425 includes a central passage 427 having a front opening, and a radial slot 426 connecting the central passage 427 to the outer surface of the tip 425. The socket receptacle 428 receives the front end 416 of the drill guide barrel 401. The remaining elements of drill guide 400-2 are the same as for the drill guide 400, as indicated by like reference numerals, and descriptions of these elements are not repeated for brevity. The operation and use of the drill guide 400-3 is the same as described above with reference to FIGS. 23-26, and the description is not repeated, for brevity.

FIGS. 35-40 show a sponge clip which can be used during any of the fixation procedures described herein (e.g., Charcot fixation procedure). The clip comprises a body 500 having a longitudinal axis 520 (shown in FIG. 40, and coinciding with section line 40-40 in FIG. 39). The body 500 has a tubular sidewall 511 integrally attached at a perimeter of the body. The body 500 has a slot 501 extending parallel to the longitudinal axis 520. The slot 501 penetrates the tubular sidewall 504 and extends part way through the body 500.

The body 500 has first and second longitudinal tubular gripping surfaces 503 and 504 within the slot 501. The second longitudinal tubular gripping surface 504 has an inner diameter that is different from an inner diameter of the first longitudinal tubular gripping surface 503. The slot 501 extends through each of the first and second longitudinal tubular gripping surfaces 503, 504. The gripping surface 503 is sized to grip a wire 412 (e.g., smooth 1.8 mm or 2 mm K-wire or olive wire), and the gripping surface 504 is sized to grip a standard (4 mm, 5 mm or 6 mm) half pin 350 (shown in FIG. 1C) of the type surgically inserted during the procedure. (Pins 350 can be inserted in the anterior side of the tibia or in the calcaneus, but wires 412 are used elsewhere. Wires can also be used in the tibia and/or calcaneus.) By inserting the wire 412 or pin 350 into the slot 501 and placing the gripping surface 503 around the wire 412 (or the griping surface 504 around the pin), the clip is quickly attached to the pin 350 or wire 412 without any tools. The clip can be positioned close to the insertion site of the wire or pin, to retain a sponge or other absorbent material against the wound site.

The body has first and second end surfaces 510, 511. The first end surface 510 is perpendicular to the longitudinal axis 520, and the second end surface 511 is oriented at an oblique angle relative to the longitudinal axis 520. The clip 500 can be attached to a wire 412 or pin 350 perpendicular to the bone, with the first end surface 510 facing toward the wound site, and the second end surface 511 facing away from the wound site. In this orientation, the first end surface 510 is parallel to the surface of the bone and holding a sponge against the wound site. Alternatively, the clip 500 can be attached to a wire 412 or pin 350 at an oblique angle with respect to the bone, with the second end surface 511 facing toward the wound site, and the first end surface 510 facing away from the wound site. In this orientation, the second end surface 511 is parallel to the surface of the bone and holding a sponge against the wound site. Thus, by selecting which end of the clip 500 to place closer to the wound site, the surgeon can maximize the area of the clip which engages the sponge (or other dressing) with the longitudinal slot 501 of the clip 500 aligned with the wire 412 or pin.

In some embodiments, the clip 500 has a counterbore 505 in the first end surface 510, to relieve pressure on the wound site. In some embodiments, the clip 500 has a counterbore 518 in the second end surface 511. The counterbores 505, 518 can assist in retaining the sponge or other dressing. In some embodiments, one or both of the counterbores 505, 518 has reinforcing ribs 517.

In some embodiments, the first longitudinal tubular gripping surface 503 is at or near the longitudinal axis 520, and the second longitudinal tubular gripping surface 504 is near a periphery of the body. In some embodiments, the second longitudinal tubular gripping surface 504 has a dimension G2 perpendicular to the longitudinal axis 520 which is larger than a dimension G1 of the first longitudinal tubular gripping surface 503 perpendicular to the longitudinal axis 520.

In some embodiments, the clip has a flat surface 513 opposite the opening of the longitudinal slot 501, to permit the surgeon or technician to push the clip onto the wire 412 or pin. The flat surface can have a key 515 to provide flexibility to open and close the clip, and to retain the clip on the pin. The remainder of the body has a round perimeter for ease of removal.

In some embodiments, the clip is formed from a single piece of a plastic, such as acrylonitrile-butadiene-styrene (ABS).

In some embodiments, a method for using the above-described apparatus for positioning a leg of a patient comprises pre-loading respective fixation devices 330, 302 in a plurality of slots (e.g., 110) of a circular fixator 100. Each fixation device 330 has a threaded bolt with a side slot 307 in a side edge thereof. The circular fixator 100 includes at least one ring e.g., 102, having the plurality of slots (e.g., 110) extending therethrough. The ring 102 has a scallop shaped recess 112a, 112b or recess pocket with a plurality of curved arcs on each of two respective interior edges that define the slot 110 therebetween. The fixation device 330 further includes a washer 340 having peripheral edges 343 adapted to fit in a respective curved arcs of the respective recess 112a, 112b of each of the edges. Alternatively, if the user wants to put the fixation device 330 in between scallops, the user can turn the washer 340 sideways, to clear the scallops.

Each threaded bolt 330 has a respective head 332 and a respective nut 334, and at least one slot (e.g., 110) of the circular fixator 100 has an opening 114a, 114b at each end thereof. The openings 114a, 114b have a size larger than a size of the head 332. The pre-loading step includes: inserting the head 332 or nut 334 of one of the fixation devices 330 though one of the openings 114a, 114b, so that the ring 102 is between the head and the nut; and inserting a plug 170 in each of the openings 114a, 114b after inserting the head 332 or nut 334, to prevent the fixation device 330 from falling out of the ring 102.

In some embodiments, at least one leg positioner 200 is attached a to an posterior end of the circular fixator without using a tool before the position step. In some embodiments, the leg positioner 200 includes a plurality of adjustable supports 204, 206, the method further comprises independently adjusting the position of each support 204, 206 without using a tool, to accommodate the leg thereon.

Some embodiments include attaching leg positioners 230, 250 to the circular fixator 100 on medial and lateral sides of a foot of the patient without using tools, so as to support the foot in a neutral or other desired position, before inserting the at least one wire 412. In some embodiments, each of the additional leg positioners 230, 250 includes a mounting device 257 having a threaded member 256. The step of attaching additional leg positioners comprises: placing the mounting device 257 so that the threaded member 256 of the mounting device extends through the slot (e.g., 138) of the ring 130 and a slot 235 (255) in an arm 231 (251) of the leg positioner 230 (250), and the head 254 of the mounting device 257 engages respective recesses (e.g., 140a, 140b) in the ring 130 on opposite sides of the slot 138 of the ring 130; and securing the mounting device 257 and the leg positioner 230, 250 to the ring 130 with a nut 252.

The circular fixator 100 is positioned around the leg. In some embodiments, the circular fixator 100 has first and second circular rings 142, 130 adapted to be positioned around the leg of the patient. The first ring 142 is greater in diameter than the second ring 130, and the positioning step includes: positioning the first ring 130 around a first portion of the leg, and positioning the second ring 142 around a second portion of the leg. The first portion of the leg has an anterior-to-posterior dimension that is greater than an anterior-to-posterior dimension of the second portion of the leg.

At least one wire 412 is inserted through leg after the pre-loading. The surgeon positions the wire drill guide 400 with the finger 404 engaging the ring (e.g., 102) of the circular fixator 100) near the insertion site, and directs the tip 405 inward toward the bone. The tip 405 can be extended to contact the bone. The surgeon inserts the wire 412. When the olive structure 413 reaches the passage 411, the tip 405 is removed, and the drill guide 400 can be backed away from the insertion site.

Each pre-loaded fixation device is slid until the side slot 348 thereof engages the at least one wire 412. To permit this step, the pre-loading includes placing the threaded bolt 330 of one of the fixation devices through the slot 110 of the circular fixator ring 102 with a nut 334 attached to the bolt, so that the nut is sufficiently loose to permit the sliding. The sliding step includes moving the one of the fixation devices 330 until the peripheral edges 343 of the corresponding washer 340 of the fixation device are received in respective curved arcs of the respective recess 112a, 112b of each of the edges.

In some embodiments, at least one of the fixation devices 330 includes a post 302 having a longitudinal slot 307 therethrough and a threaded member 314, and the pre-loading includes: placing the threaded bolt 330 of one of the fixation devices through a slot 307 in the post 302 of that fixation device, placing respective nuts 316 on the threaded member 314 of the post 302 and the threaded bolt 330, and placing the fixation device 330 in the ring 102, so that the threaded member 314 of the post extends through the slot 110 of the ring 102, with the nut 316 on the threaded member 314 of the post 302 sufficiently loose to permit the sliding. The ring 102 has a scallop shaped recess 112*a*, 112*b* with a plurality of curved arcs on each of two respective interior edges that define the slot of the ring therebetween, the post 302 has a mounting surface 303 configured to fit in a respective one of the curved arcs of the scallop-shaped recess 112*a*, 112*b* on each respective side of the slot 110 in the ring 102, and the step of sliding includes sliding the threaded member 314 of the post 302 within the slot 110 until the side slot 348 of the threaded bolt 330 engages the wire 412 and the mounting surface 303 of the post 302 is received by a pair of the curved arcs of the scallop shaped recess 112*a*, 112*b*.

In some embodiments, the post 302 has a plurality of grooves 306 on a side face thereof, and the fixation device further comprises a washer 340 having a ridge 342; the method further comprises: inserting the threaded bolt 330 through the washer 340, wherein the step of placing the threaded bolt 330 through the slot 307 in the post 302 includes engaging one of the grooves 306 with the ridge 342.

The fixation devices 330, 350 are secured by tightening, so as to secure the engaged wire 412 to the circular fixator. In some embodiments, the securing includes tightening a head 332 or a nut 334 of at least one of the fixation devices 330 using a ratcheting wrench 600 having a socket member 602 with an open end 603 in the socket member to fix the fixation device 330; and passing the wire 412 or pin 350 through the open end 603 of the socket 602 after the tightening to remove the wrench.

Once the wires 412 and/or pins 350 are inserted, the leg positioners 200, 230, 250 are removed. The side leg positioners 230, 250 are removed by loosening the corresponding nuts 252 from the mounting devices 257, and releasing the positioners 230, 250. The removal of the leg positioner assembly 200 includes retracting each support device 204, 206 until the corresponding neck portion 207*n* of the corresponding arm 207 is aligned in between the retaining members 221; and sliding the support members 204, 206 out through the passage 205 between the retaining members in a direction perpendicular to the direction of the retraction (and parallel to the front face 201*a* of the body 201 of the leg positioner assembly 200. Once the support members 204, 206 are removed, the body 201 of the leg positioner assembly 200 can be removed by unscrewing the knob 218.

In some embodiments, following insertion of at least one wire 412 or pin 350, a first sponge or other dressing (not shown) is held at a first wound site of the patient using a first clip 500 having a longitudinal slot 501 in a side surface of the first clip 500 for receiving and gripping the wire 412 or pin 350 to position the sponge.

The first clip 500 has a flat surface 510 at a first end thereof for engaging the sponge with a longitudinal axis 520 of the first clip 500 approximately normal to a tissue of the patient at the first wound site. The first clip 500 has an angled surface 511 at a second end opposite the first end, and the method further comprises: holding a second sponge (not shown) at a second wound site of the patient using a second clip 500 for receiving and gripping a second wire 412 to position the second sponge. The second clip 500 is identical to the first clip. The angled surface 511 of the second clip engages the second sponge with a longitudinal axis 520 of the second clip at oblique angle relative to a tissue of the patient at the second wound site.

In some embodiments, the first clip has first and second tubular gripping surfaces 503, 504 within the longitudinal slot. The at least one wire 412 is gripped by the first tubular gripping surface 503. The second tubular gripping surface 504 has a different size from the first tubular griping surface 503. The second wound site has a half pin 350 or a second wire 412 inserted therein, the half pin 350 or second wire 412 has a different diameter from the at least one wire, and the half pin 350 or second wire is gripped by the second tubular gripping surface 504 of the second clip.

Figure 41:
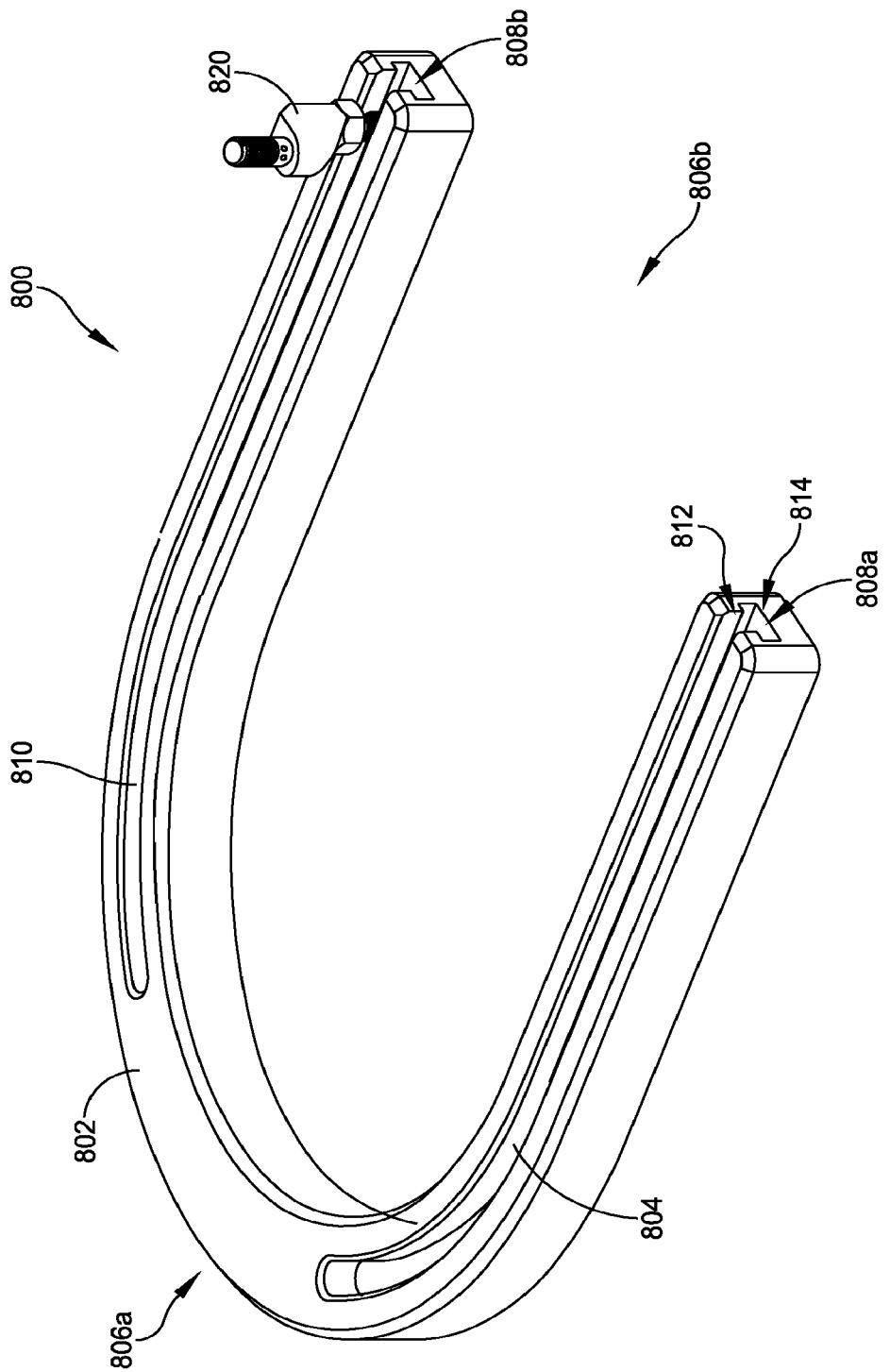
FIG. 41 is a side elevation view of one embodiment of a rocker plate, according to some embodiments.
Figure 42:
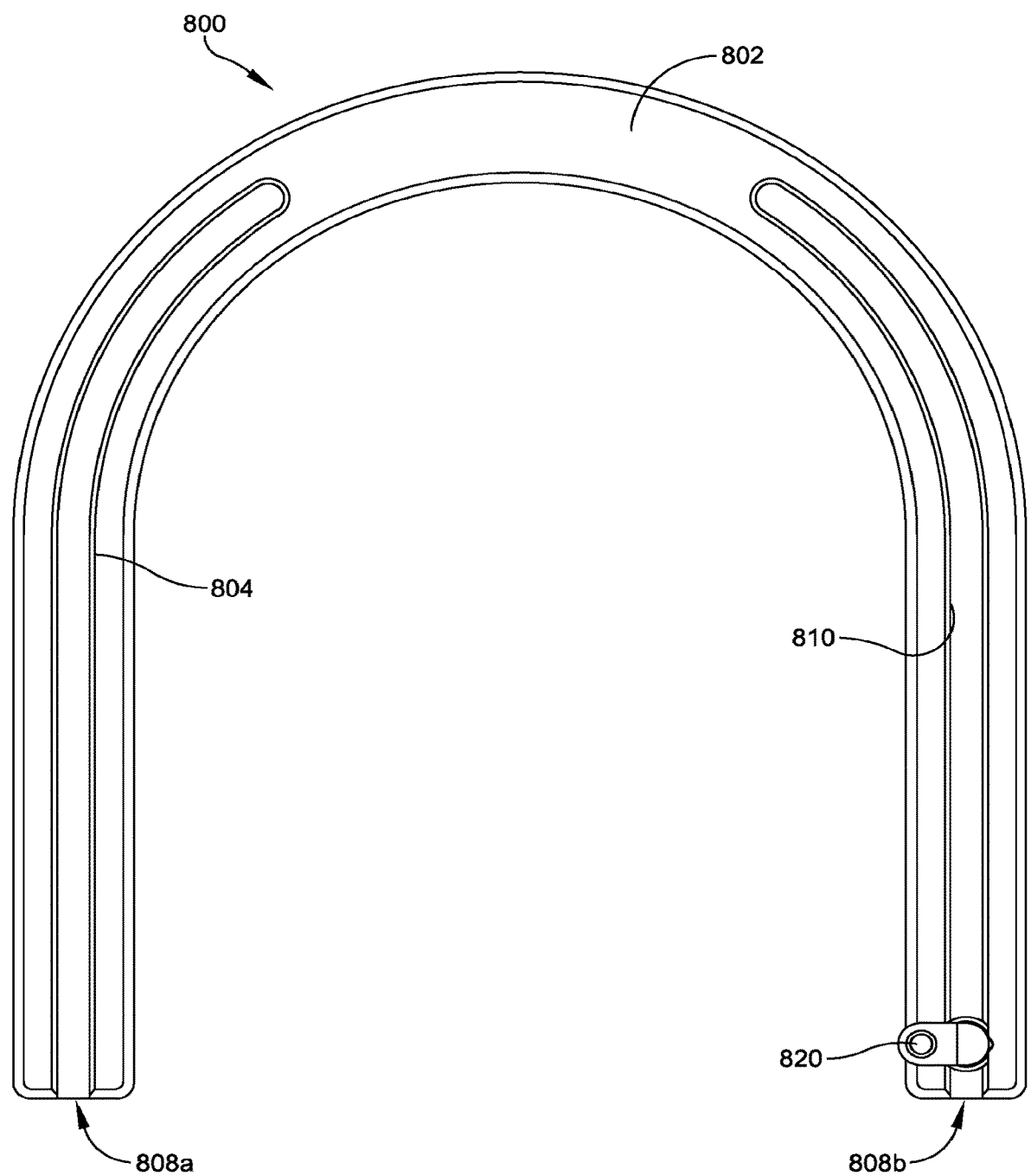
FIG. 42 is a plan view of the rocker plate shown in FIG. 41.
Figure 43:
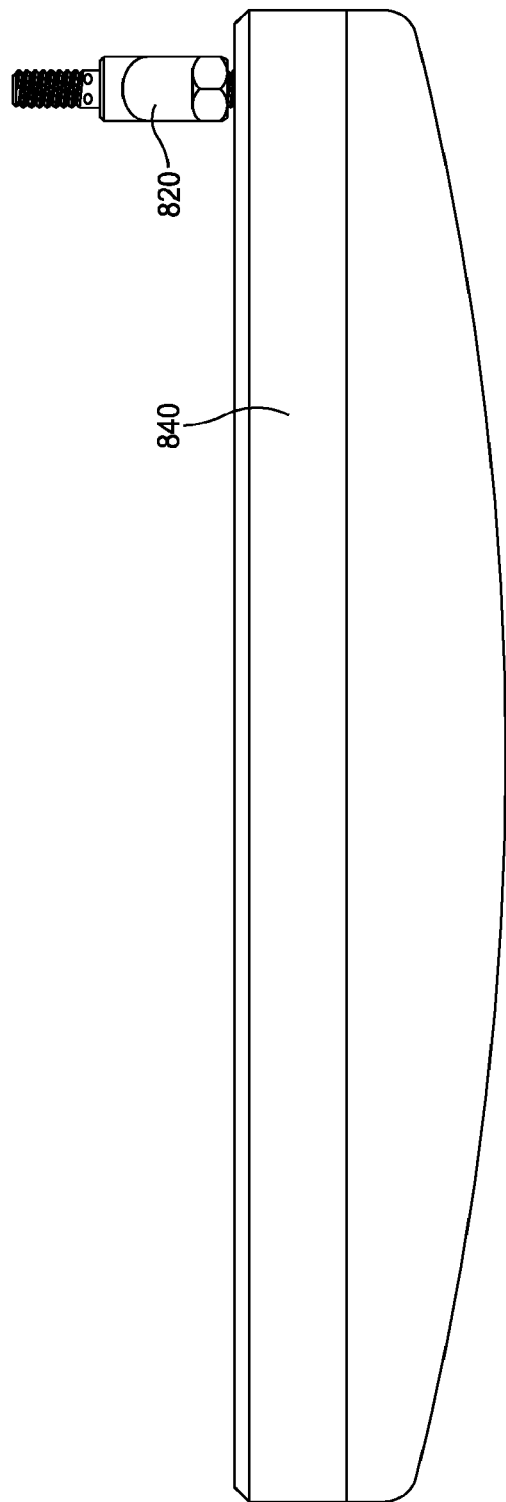
FIG. 43 is a side view of the rocker plate shown in FIG. 41.

In some embodiments, a rocker plate can be coupled to the ring 102 to support the circular fixator 100, 700. FIGS. 41-43 illustrate one embodiment of a rocker plate 800 configured to couple to the ring 102 of a circular fixator 100, 700 as described herein. The rocker plate 800 includes a frame 802 having a closed end 806*a* and an open end 806*b*. In some embodiments, the frame 802 has an elongated, semi-circular (or horseshoe) design, although it will be appreciated that the frame 802 can have any suitable shape. Although a single frame rocker plate 800 is illustrated, it will be appreciated that the rocker plate 800 can comprise one or more unconnected frame components, such as, for example, a first frame component and a second frame component. The rocker plate 800 is configured to fit multiple sizes of circular fixators 100, 700.

In some embodiments, the frame 802 defines one or more slots 804, 810 extending from a top surface into the frame 802. For example, the frame 802 illustrated in FIGS. 41-43 has a first slot 804 and a second slot 810. In some embodiments, the slots 804, 810 are T-slots having an upper portion 812 having a first width and a lower portion 814 having a second width greater than the first width. Although embodiments are illustrated herein including T-slots, it will be appreciated that the slots 804, 810 can include any suitable shape configured to allow movement of a slider 820 within the slot 804, 810. In some embodiments, the slots 804, 810 are sized and configured to allow movement of the slider 820 within the slot but prevent rotation of the slider 820.

Figure 44:
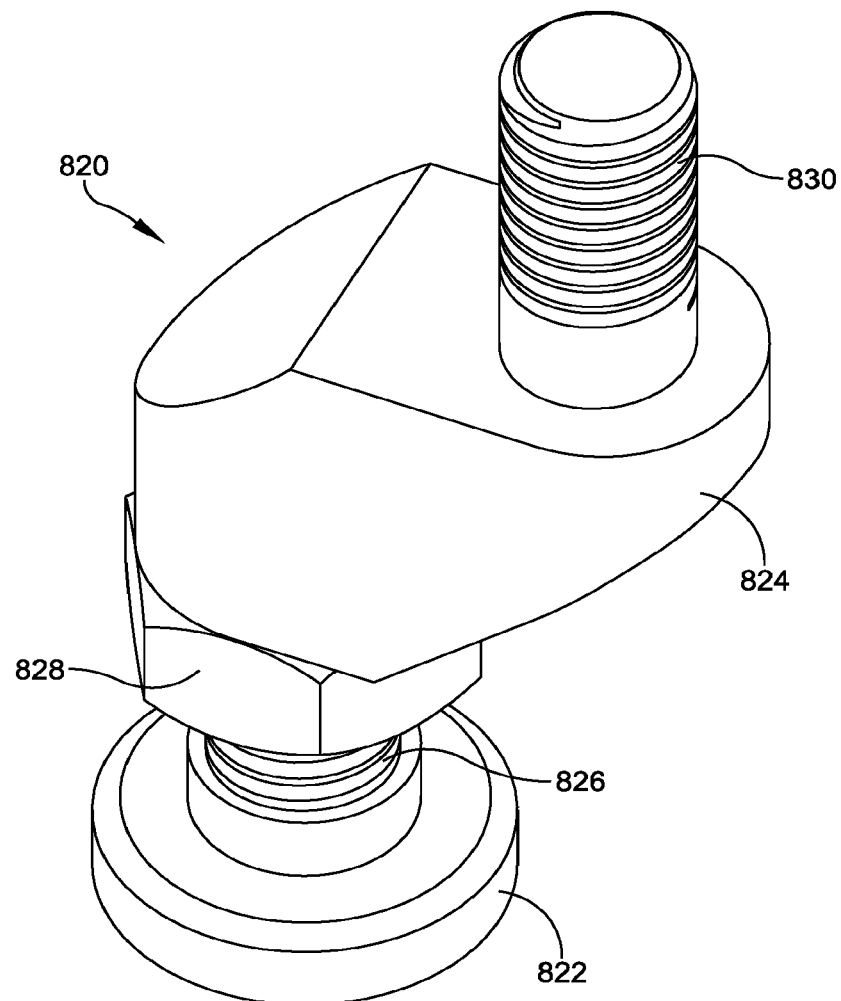
FIG. 44 is a side elevation view of a slider, according to some embodiments.
Figure 45:
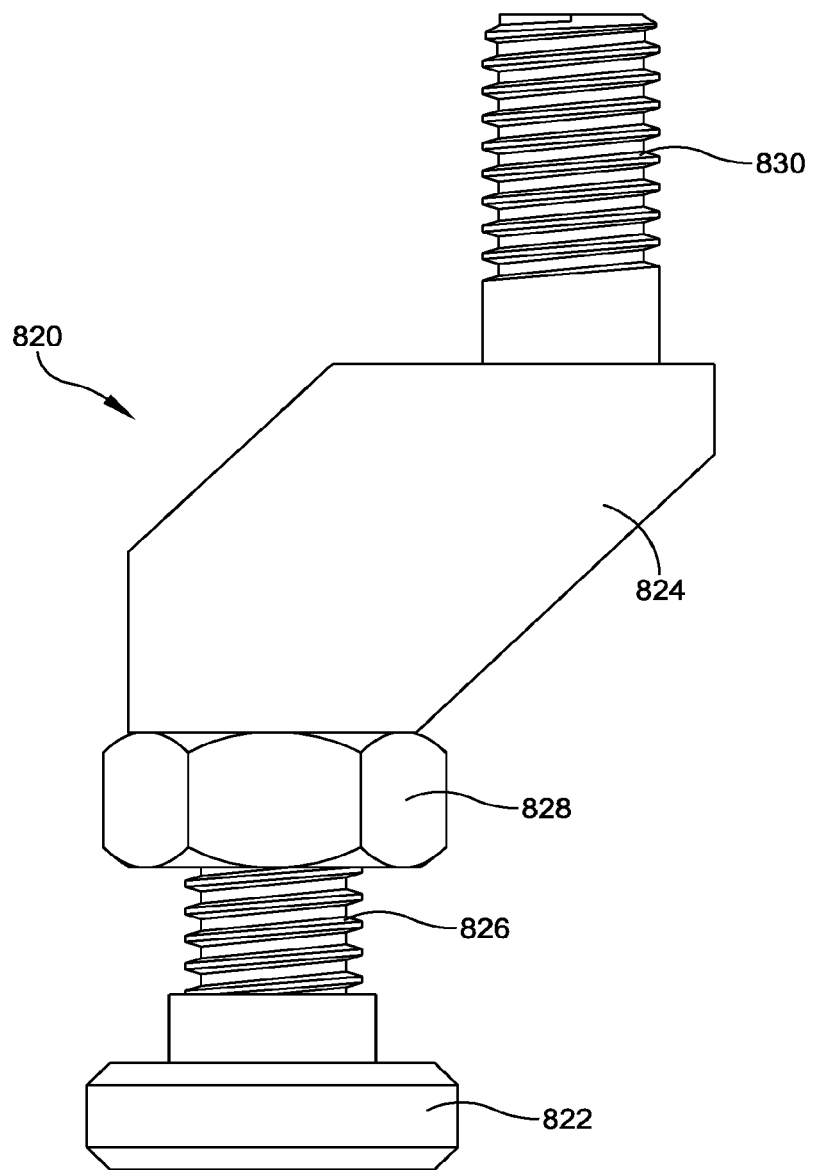
FIG. 45 is a side view of the slider shown in FIG. 45.

In some embodiments, the slots 804, 810 are sized and configured to receive a plurality of sliders 820 therein. The slots 804, 810 are coupled to an opening 808*a*, 808*b* at each end of the frame 802. The openings 808*a*, 808*b* are sized and configured such that the plurality of sliders 820 can be inserted into the T-slots 804, 810 through the openings 808*a*, 808*b*. FIG. 44 illustrates one embodiment of a slider 820. Each of the sliders 820 includes a slider portion 822 coupled to a support portion 824 by a first elongate shaft 826. The slider portion 822 has a diameter less than or equal to the second width of the lower portion 814 of the T-slots 804, 810 but greater than the first width of the upper portion 812. In some embodiments, the slider portion 822 comprises a disc (slider plate) sized and configured to slide within the lower portion 814 of the T-slot. The first elongate shaft 826 has a diameter less than the diameter of the upper portion 812, and extends from the slider portion 822 through the upper portion 812 and above the top surface of the frame 802 when the slider 820 is inserted into the slot 804, 810. The slider 820 can be slideably moved within the T-slots 804, 810 to position the rocker plate 800 and/or the sliders 820 with respect to a bottom ring 102 of a circular fixator 100, 700.

In some embodiments, the first elongate shaft 826 includes a plurality of threads sized and configured to receive a nut 828. The nut 828 can be tightened to fix the slider 820 in place with respect to the rocker plate 800. In some embodiments, the T-slot 804, 810 allows the slider 820 and/or the rocker plate 800 to be positioned with respect to the circular fixator 100, 700. In some embodiments, one or more spacers (not shown) can be positioned between the nut 828 and the frame 802 and/or the nut 828 and the support portion 824. The spacers can increase a spacing between the rocker plate 800 and a circular fixator 100, 700 coupled thereto.

The support portion 824 is sized and configured to interface with and support the bottom ring 102 of the circular fixator 100, 700. A second elongate shaft 830 extends from a proximal end of the support portion 824. The second elongate shaft 830 is sized and configured to extend through a slot 104, 110 formed in the lower ring 102 of the circular fixator 100, 700. In some embodiments, the second elongate shaft 830 includes a plurality of threads. The plurality of threads are configured to receive a nut thereon (not shown) to couple the rocker plate 800 to the circular fixator 100, 700.

In some embodiments, a sole 840 is coupled to a bottom edge of the rocker plate 800. The sole 840 comprises a molded and/or machined cover that extends from a bottom surface of the rocker plate 800 at least partially over each of the side walls of the rocker plate 800. The sole 840 can comprise any suitable material, such as, for example, a plastic material, a rubber material, a composite material, and/or any other suitable material. The sole 840 can include an overmolded and/or a machined sole attached to the frame 802. The sole 840 does not extend over the openings 808a, 808b or the slots 804, 810 and does not interfere with movement of the sliders 820 within the T-slots 804, 810. In some embodiments, the sole 840 includes a non-slip surface.

Figure 46:
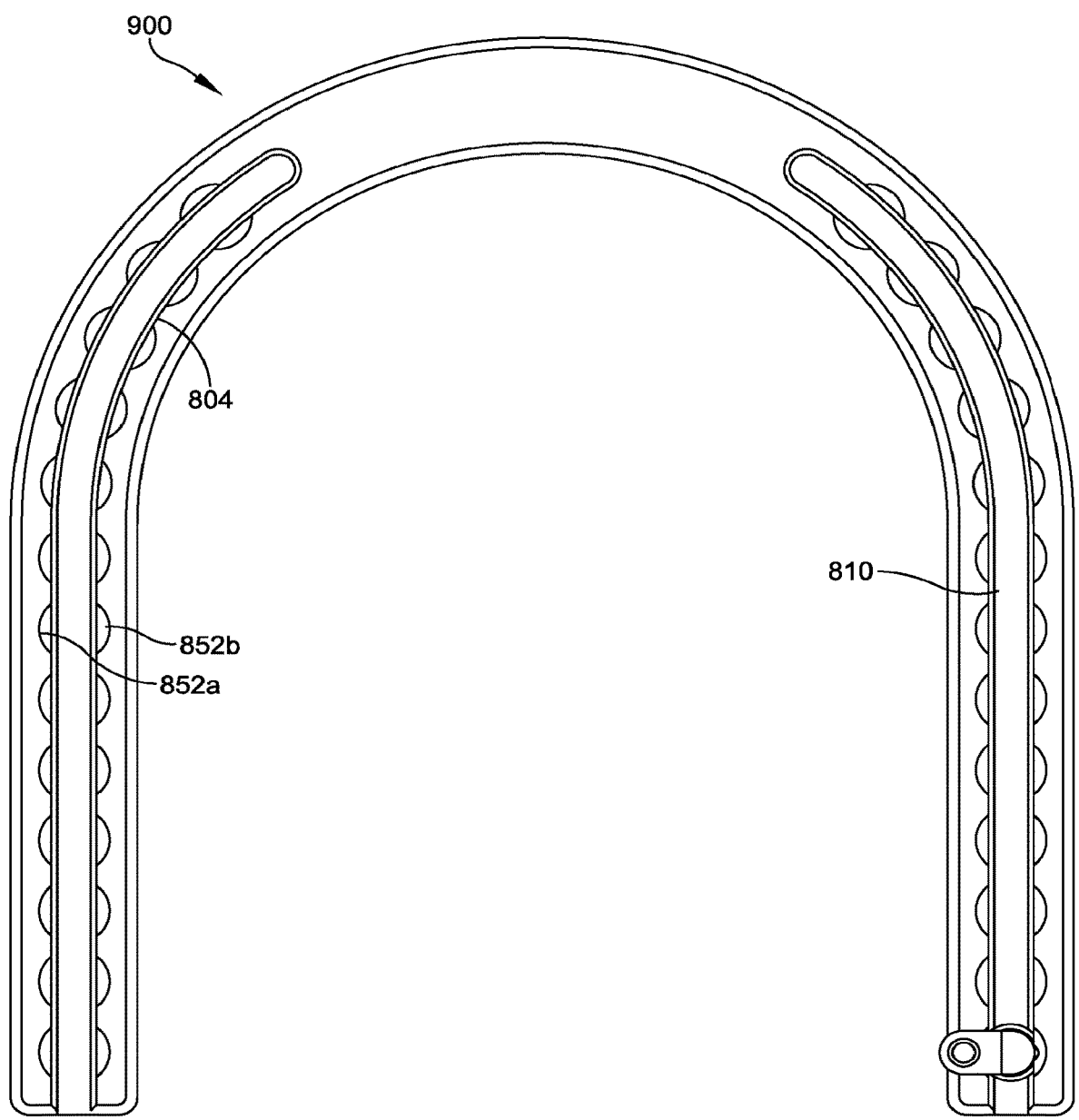
FIG. 46 is a plan view of the rocker plate having a plurality of counterbores formed therein, according to some embodiments.

FIG. 46 illustrates one embodiment of a rocker plate 900 having a plurality of scallop-shaped recesses 852a, 852b formed thereon. The plurality of scallop-shaped recesses 852a, 852b are formed about the periphery of the T-slots 804, 810. The scallop-shaped recesses 852, 852b are similar to the scallop-shaped recesses 106a, 106b formed in the ring 102 and prevent slipping of the slider 820 relative to the T-slots 804, 810. The scallop-shaped recesses 852a, 852b prevent movement or slippage of the rocker plate 800 with respect to the lower ring 102.

Figure 47:
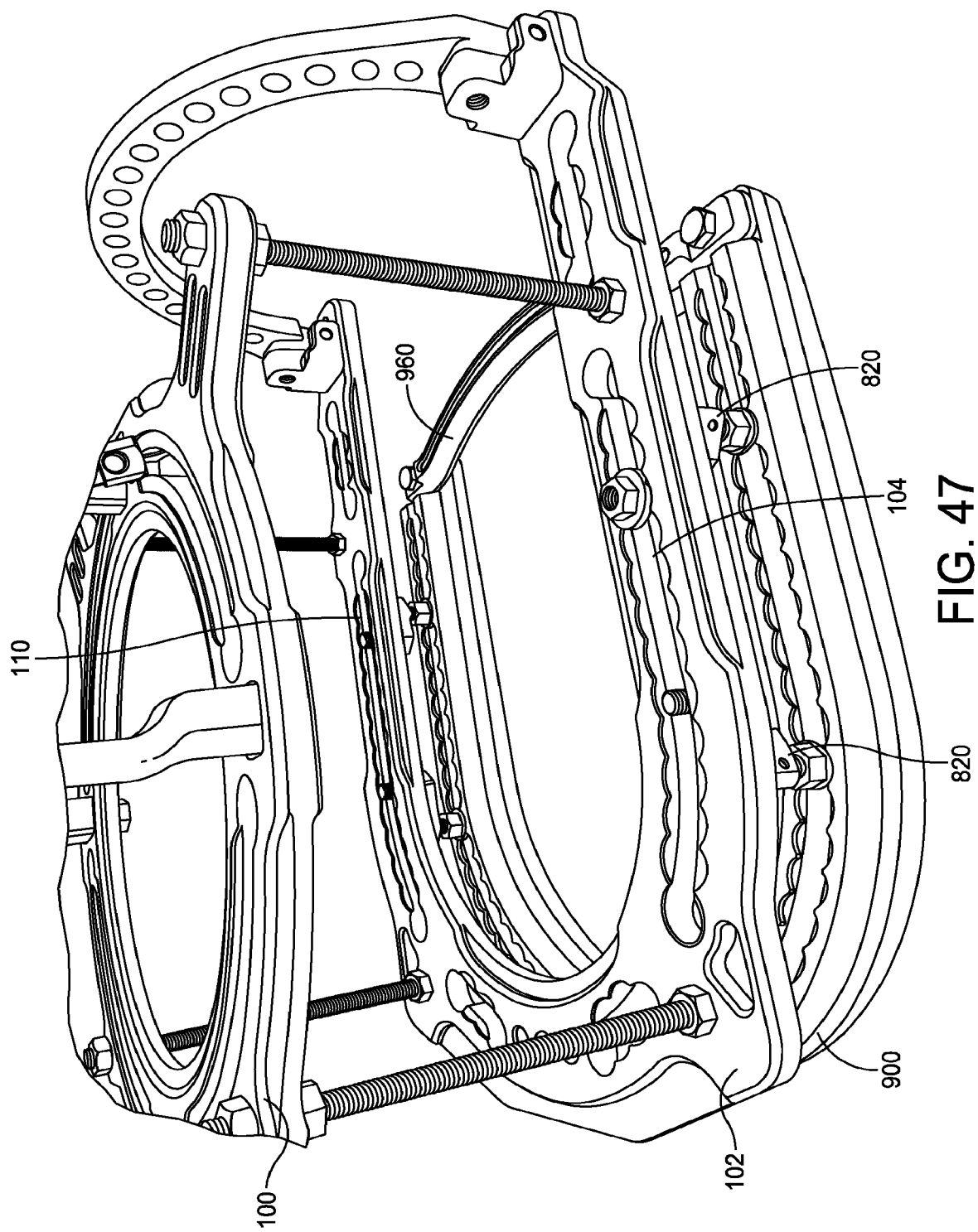
FIG. 47 is a side elevation view of the rocker plate of FIG. 46 coupled to a circular fixator, according to some embodiments.

FIG. 47 illustrates one embodiment of the rocker plate 900 coupled to an embodiment of the circular fixator 100. The rocker plate 900 includes a plurality of sliders 820 inserted into the T-slots 804, 810 formed therein. The bottom ring 102 of the circular fixator 100 is supported at a predetermined spacing by the support portion 824 of each of the sliders 820. The predetermined spacing can be adjusted to accommodate patients with varying foot sizes. The second elongated shaft 830 of each of the sliders 820 extends through the slots 104, 110 formed in the ring 102. A nut 854 is threadably coupled over a proximal end of the elongate shaft 830 to maintain the circular fixator 100 and the rocker plate 900 in a fixed position.

In some embodiments, a securing bar 960 is coupled to a proximal end of the rocker plate 900. The securing bar 960 maintains the first and second ends of the rocker plate 900 at a fixed spacing and prevents the first and second ends of the rocker plate 900 from twisting or expanding during an operation. In some embodiments, the securing bar 960 is positioned to prevent the sliders 820 from sliding out of the T-slots 804, 810 formed in the frame 802. For example, as shown in FIG. 47, in some embodiments, the securing bar 960 effectively covers the openings 808a, 808b formed in the slots 804, 810, preventing the sliders 820 from sliding out of the T-slots 804, 810. In some embodiments, a pin (not shown) is inserted into the openings 808a, 808b to prevent the sliders 820 from sliding out of the slots 804, 810.

Although the subject matter has been described in terms of exemplary embodiments, it is not limited thereto. Rather, the appended claims should be construed broadly, to include other variants and embodiments, which may be made by those skilled in the art

What is claimed is:

1. A rocker plate assembly, comprising:
    a unitary U-shaped body including:
        a first side member having a first end,
        a second side member having a second end, and
        a curved portion integrally attached to the first side member and the second side member, the first and second side members each have at least one T-shaped slot extending into the body; and
    a sole having a first sidewall and a second sidewall each extending over sidewalls of the body, the sole being coupled to a bottom surface of the body;
    a securing member covering openings of the slots;
    a plurality of sliders, each having:
        a slider plate slidably retained in a respective bottom of a respective one of the T-shaped slots,
        a first shaft slidably retained in a respective top of the respective one of the T-shaped slots,
        a support attached to the first shaft, and
        a second shaft attached to the support, the second shaft offset from the first shaft.

2. The rocker plate assembly of claim 1, wherein the sole comprises a polymer.

3. The rocker plate assembly of claim 2, wherein the top surface of the body includes a plurality of scallop-shaped recesses formed adjacent each of the slots.

4. The rocker plate assembly of claim 3, wherein the first shaft is threaded, the assembly further comprising a first nut threadably received on the first shaft for gripping a respective one of the side members between the first nut and the slider plate.

5. The rocker plate assembly of claim 4, wherein the second shaft is threaded, the assembly further comprising a second nut threadably received on the second shaft for gripping a ring of a circular fixator between the second nut and the support.

6. A fixation system, comprising:
    at least two rings, each ring having a first face, a second face, and a slot penetrating from the first face to the second face;
    a plurality of members joining each one of the rings to an adjacent one of the rings;
    a rocker plate including:
        a first side member defining a slot;
        a second side member defining a slot; and
        a connecting portion attached to the first side member and second side member;
    a sole having a first sidewall, and a second sidewall, and being coupled to a rocker plate body, the first and second sidewalls extend over sidewalls of the rocker plate body, and a securing member is attached to the rocker plate body; and
    a plurality of sliders slidably retained in the slots, each slider having a first shaft received by a respective one of the slots of the first or second side members and a second shaft received by a slot of a bottom one of the rings, wherein the second shaft is offset from the first shaft, wherein the securing member covering openings of the slots so as to prevent the sliders from sliding out of the slots.

7. The fixation system of claim 6, wherein each of the sliders comprises a support portion, the first shaft attached adjacent a first end of the support portion, and the second shaft attached adjacent a second end of the support portion.

8. The fixation system of claim 7, wherein:
   the slots of the first and second side members are T-shaped, each slider comprises a disc and a nut, each disc is received in a bottom of one of the slots of a respective one of the first or second side member, and the first and second side members are gripped between the disc and nut of each respective slider.

\* \* \* \* \*